(12) United States Patent
Velazquez-Palafox et al.

(10) Patent No.: US 12,399,170 B2
(45) Date of Patent: Aug. 26, 2025

(54) CYTOMETRIC BEAD ARRAY ANALYSIS

(71) Applicant: Becton, Dickinson and Company, Franklin Lakes, NJ (US)

(72) Inventors: Miguel Velazquez-Palafox, Franklin Lakes, NJ (US); Ian Taylor, Franklin Lakes, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1362 days.

(21) Appl. No.: 16/851,651

(22) Filed: Apr. 17, 2020

(65) Prior Publication Data
US 2020/0333330 A1    Oct. 22, 2020

Related U.S. Application Data

(60) Provisional application No. 62/836,705, filed on Apr. 21, 2019.

(51) Int. Cl.
*G01N 33/53* (2006.01)
*G01N 15/06* (2006.01)
*G01N 15/1434* (2024.01)
*G01N 15/075* (2024.01)
*G01N 15/149* (2024.01)

(52) U.S. Cl.
CPC ............ *G01N 33/53* (2013.01); *G01N 15/06* (2013.01); *G01N 15/1434* (2013.01); *G01N 15/075* (2024.01); *G01N 15/149* (2024.01)

(58) Field of Classification Search
CPC .... G01N 33/53; G01N 15/06; G01N 15/1434; G01N 2015/0693
See application file for complete search history.

(56) References Cited

U.S. PATENT DOCUMENTS

| | | |
|---|---|---|
| 6,449,562 B1 * | 9/2002 | Chandler ............... G16B 50/10 435/6.12 |
| 10,091,279 B2 | 10/2018 | Stadnisky |
| 10,438,120 B2 | 10/2019 | Simm et al. |
| 10,601,902 B2 | 3/2020 | Stadnisky |
| 10,616,219 B2 | 4/2020 | Stadnisky et al. |
| 10,713,572 B2 | 7/2020 | Simm et al. |
| 10,783,439 B2 | 9/2020 | Simm et al. |
| 11,573,182 B2 | 2/2023 | Roederer et al. |
| 2018/0165414 A1 | 6/2018 | Almarode et al. |
| 2020/0105376 A1 | 4/2020 | Lai et al. |

OTHER PUBLICATIONS

BD Biosciences, 2012, BD Cytometric Bead Array, Multiplexed Bead-Based Immunoassays, 16 pp.
Becton Dickinson et al., Jul. 1, 2011, FCAP Array™ Software Version 3.0 User's Guide, 130 pp.
International Search Report and Written Opinion dated Jul. 28, 2020 in application No. PCT/US2020/028681.

* cited by examiner

*Primary Examiner* — Gailene Gabel
(74) *Attorney, Agent, or Firm* — KNOBBE, MARTENS, OLSON & BEAR, LLP

(57) ABSTRACT

Disclosed herein include systems, devices, and methods for cytometric bead array (CBA) analysis. After receiving user selections of a reporter fluorescent dye and clustering fluorescent dyes, gates for CBA event data corresponding to analytes in samples and standard curves for the analytes can be determined. Concentrations of the analytes in the samples can be determined using the standard curves.

19 Claims, 33 Drawing Sheets

FIG. 6B

Enter Concentrations

Human C3a

| Sample | Yellow-A Median | Concentration (ng/mL) |
|---|---|---|
| Standard_10_Std10.fcs | 467.85 | 2500.0 |
| Standard_09_Std09.fcs | 361.9 | 1250.0 |
| Standard_08_Std08.fcs | 228.76 | 625.0 |
| Standard_07_Std07.fcs | 122.71 | 313.0 |
| Standard_06_Std06.fcs | 57.25 | 157.0 |
| Standard_05_Std05.fcs | 27.02 | 79.0 |
| Standard_04_Std04.fcs | 13.28 | 40.0 |
| Standard_03_Std03.fcs | 8.13 | 20.0 |
| Standard_02_Std02.fcs | 7.77 | 10.0 |

FIG. 6G

7 : y = d+(a-d)/(1+(x/c)^b) ; 4 Parameter Logistic (Rodb... *

0 : y = a+b*x ; Straight Line

1 : y = a+b*x+c*x^2 ; 2nd Degree Polynomial

2 : y = a+b*x+c*x^2+d*x^3 ; 3rd Degree Polynomial

5 : y = a*x^b ; Power

7 : y = d+(a-d)/(1+(x/c)^b) ; 4 Parameter Logistic (Rodbard)

8 : y = b*(x-a)^c*exp(-(x-a)/d) ; Gamma Variate

| Ancestry Subset Statistic For | CBA_SIZE Human C5a Median CBA_Human C5a | CBA_SIZE Human C3a Median CBA_Human C3a | CBA_SIZE Human C4a Median CBA_Human C4a |
|---|---|---|---|
| Standard_01_S... | 5.20 | 7.35 | 7.07 |
| Standard_02_S... | 12.5 | 13.3 | 12.2 |
| Standard_03_S... | 17.3 | 14.1 | 15.0 |
| Standard_04_S... | 34.6 | 26.8 | 32.0 |
| Standard_05_S... | 72.6 | 66.2 | 64.5 |
| Standard_06_S... | 149 | 167 | 169 |
| Standard_07_S... | 354 | 407 | 414 |
| Standard_08_S... | 680 | 812 | 815 |
| Standard_09_S... | 1346 | 1334 | 1398 |
| Standard_10_S... | 2127 | 1745 | 1735 |
| S001_S001_001... | 156 | 170 | 175 |
| S002_S002_001... | 349 | 425 | 431 |
| S003_S003_001... | 728 | 864 | 894 |
| S007_S007_001... | 7.08 | 12.1 | 9.84 |
| S008_S008_001... | 13.8 | 14.5 | 22.9 |
| S009_S009_001... | 20.8 | 16.8 | 34.7 |
| S010_S010_001... | 40.7 | 44.3 | 73.1 |
| S011_S011_001... | 91.4 | 106 | 169 |
| S012_S012_001... | 191 | 284 | 392 |
| S013_S013_001... | 384 | 613 | 778 |
| S014_S014_001... | 898 | 1338 | 1575 |
| S015_S015_001... | 1514 | 1819 | 1968 |
| S016_S016_001... | 2457 | 2485 | 2389 |
| S017_S017_001... | 176 | 256 | 317 |
| S018_S018_001... | 396 | 631 | 731 |
| S019_S019_001... | 888 | 1279 | 1436 |

Table_CBA_Analytes_Summary

| | CBA_Beads Human C5a Median CBA_Human C5a | CBA_Beads Human C3a Median CBA_Human C3a | CBA_Beads Human C4a Median CBA_Human C4a |
|---|---|---|---|
| REF_01_zero.fcs | 8.19 | 11.7 | 3.49 |
| REF_02_10_10_4.fcs | 14.7 | 13.1 | 13.3 |
| REF_03_20_20_8.fcs | 15.5 | 18.9 | 16.6 |
| REF_04_40_40_16.fcs | 29.1 | 40.2 | 36.0 |
| REF_05_80_80_32.fcs | 147 | 53.5 | 59.1 |
| REF_06_156_156_62.5.fcs | 275 | 130 | 181 |
| REF_07_312.5_312.5_12... | 477 | 466 | 373 |
| REF_08_625_625_250.fcs | 1025 | 800 | 738 |
| REF_09_1250_1250_500.fcs | 1807 | 1067 | 1764 |
| REF_10_2500_2500_1000... | 2478 | 2181 | 1385 |
| REF_S001_df_16.fcs | 188 | 194 | 187 |
| REF_S002_df_8.fcs | 798 | 480 | 240 |
| REF_S003_df_4.fcs | 2139 | 542 | 798 |
| S007_S007_test_0.fcs | 13.4 | 16.9 | 4.71 |
| S008_S008_test_10_10_4.fcs | 54.4 | 11.0 | 9.24 |
| S009_S009_test_20_20_8.fcs | 18.5 | 23.1 | 39.1 |
| S010_S010_test_40_40_16.fcs | 165 | 35.5 | 30.5 |
| S011_S011_test_80_80_32.fcs | 156 | 84.8 | 182 |
| S012_S012_test_156_156_6... | 323 | 238 | 390 |
| S013_S013_test_312_5_312... | 1676 | 410 | 411 |
| S014_S014_test_625_625_2... | 2897 | 764 | 1282 |
| S015_S015_test_1250_1250... | 6393 | 961 | 1535 |
| S016_S016_test_2500_2500... | 3776 | 2458 | 1795 |
| S017_S017_test_df_16.fcs | 290 | 384 | 165 |
| S018_S018_test_df_8.fcs | 926 | 420 | 671 |
| S019_S019_test_df_4.fcs | 3174 | 738 | 1090 |
| Mean | 1126 | 482 | 518 |
| SD | 1557 | 630 | 594 |

FIG. 11D

CYTOMETRIC BEAD ARRAY ANALYSIS

INCORPORATION BY REFERENCE TO RELATED APPLICATIONS

The present application claims priority under 35 U.S.C. § 119(e) to U.S. Provisional Application No. 62/836,705, filed on Apr. 21, 2019. The content of this related application is herein expressly incorporated by reference in its entirety.

BACKGROUND

Field

This disclosure relates to relates generally to the field of automated particle assessment, and more particularly to sample analysis and particle characterization methods.

Background

Particle analyzers, such as flow cytometers, can enable the characterization of particles on the basis of electro-optical measurements such as light scatter and fluorescence. In a flow cytometer, for example, particles, such as molecules, analyte-bound beads, or individual cells, in a fluid suspension are passed by a detection region in which the particles are exposed to an excitation light, typically from one or more lasers, and the light scattering and fluorescence properties of the particles are measured. Particles or components thereof typically are labeled with fluorescent dyes to facilitate detection. A multiplicity of different particles or components can be simultaneously detected by using spectrally distinct fluorescent dyes to label the different particles or components. Different cell types can be identified by their light scatter characteristics and fluorescence emissions resulting from labeling various cell proteins or other constituents with fluorescent dye-labeled antibodies or other fluorescent probes. The data obtained from an analysis of cells (or other particles) by multi-color flow cytometry are multidimensional, where each cell corresponds to a point in a multidimensional space defined by the parameters measured. Populations of cells or particles can be identified as clusters of points in the data space.

SUMMARY

Disclosed herein include embodiments of a method for cytometric bead array analysis. In some embodiments, the method is under control of a processor (e.g., a hardware processor or a virtual processor) and comprises: receiving cytometric bead array (CBA) event data of a plurality of events corresponding to a plurality of samples and a plurality of standards. Each of the plurality of events can be associated with (1) a reporter fluorescent intensity of a reporter fluorescent dye associated with a reporter antibody, and (2) a clustering fluorescent intensity of a clustering fluorescent dye associated with a bead in the CBA event data. The method can comprise: receiving user selections of the reporter fluorescent dye and the clustering fluorescent dye. The method can comprise: determining a first plurality of gates for CBA event data, based on the clustering fluorescent intensity of each of the plurality of events, to determine events of interest and corresponding analytes. The method can comprise: receiving user inputs of an initial concentration and a dilution factor of each of the plurality of analytes. The method can comprise: receiving a user selection of a regression function of a plurality of regression functions. The method can comprise: for each of the plurality of analytes, determining a standard curve of correspondence of reporter fluorescent intensities and concentrations of the analyte using the initial concentration, the dilution factor, the regression function, and the reporter fluorescent intensities corresponding to the analyte in standard CBA event data of the CBA event data corresponding to the plurality of standards. The method can comprise: for each sample of a plurality of samples, determining a sample concentration of each of a plurality of analytes based on the reporter fluorescent intensity in sample CBA event data of the CBA event data corresponding to the analyte using the regression function. The method can comprise: generating for each analyte of the plurality of analytes, a plot of the standard curve and the correspondence of the reporter fluorescent intensities and the concentrations of the analyte, and/or (2) a table comprising a sample concentration of each of the plurality of analytes for each of the plurality of samples.

In some embodiments, the method comprises: under control of a processor: receiving cytometric bead array (CBA) event data of a plurality of events corresponding to a plurality of samples and a plurality of standards, wherein each of the plurality of events is associated with (1) a reporter fluorescent intensity of a reporter fluorescent dye associated with a reporter antibody, and (2) a clustering fluorescent intensity of a clustering fluorescent dye associated with a bead in the CBA event data, wherein the plurality of standards is associated with an initial concentration and a dilution factor of each of the plurality of analytes; determining a first plurality of gates for CBA event data, based on the clustering fluorescent intensity of each of the plurality of events, to determine events of interest and corresponding analytes of the plurality of analytes; receiving a user selection of a regression function of a plurality of regression functions; for each of the plurality of analytes, determining a standard curve of correspondence of reporter fluorescent intensities and concentrations of the analyte using the initial concentration, the dilution factor, the regression function, and the reporter fluorescent intensities corresponding to the analyte in standard CBA event data of the CBA event data corresponding to the plurality of standards; for each sample of a plurality of samples, determining a sample concentration of each of a plurality of analytes based on the reporter fluorescent intensity in sample CBA event data of the CBA event data corresponding to the analyte using the regression function; and/or generating (1) for each analyte of the plurality of analytes, a plot of the standard curve and the correspondence of the reporter fluorescent intensities and the concentrations of the analyte, and (2) a table comprising a sample concentration of each of the plurality of analytes for each of the plurality of samples.

In some embodiments, a sample of the plurality of samples comprises the plurality of analytes each at a sample concentration. A standard of the plurality of standards can comprise each of the plurality of analytes each at a standard concentration. Two standards of the plurality of standards can comprise two different standard concentrations of each of the plurality of analytes.

In some embodiments, the method comprises: requesting a user selection of a CBA assay of a plurality of CBA assays for determining the quantities of the plurality analytes or a user input of the plurality of analytes. The method can comprise: receiving the user selection of the CBA assay of the plurality of CBA assays for determining the quantities of the plurality analytes. The method can comprise: receiving the user input of the plurality analytes.

In some embodiments, the method comprises: receiving user selections of the standard CBA event data of the CBA event data corresponding to the plurality of standards. The method can comprise: receiving user selections of the sample CBA event data of the CBA event data corresponding to the plurality of samples and the standard CBA event data of the CBA event data corresponding to the plurality of standards.

In some embodiments, each of the plurality of events is associated with (3) a forward scatter value, and (4) a side scatter value in the CBA event data. The method can comprise: determining a second plurality of gates for the CBA event data, based on the forward scatter value and the side scatter value of each of the plurality of events, to determine the events of interest.

In some embodiments, the bead is associated with a clustering antibody capable of binding to an analyte of the plurality of analytes. Two beads of the beads can comprise different (1) quantities of the clustering fluorescent dye that identify the two beads and clustering antibodies capable of binding to two different analytes of the plurality of analytes.

In some embodiments, determining the standard curve comprises: determining the standard curve of correspondence of the reporter fluorescent intensities and the concentrations of the analyte using the initial concentration, the dilution factor, the regression function, and median reporter fluorescent intensities corresponding to the analyte at different standard concentrations in the standard CBA event data of the CBA event data corresponding to the plurality of standards.

In some embodiments, determining the sample concentration comprises determining the sample concentration of each of a plurality of analytes based on a median reporter fluorescent intensity in the CBA event data corresponding to the analyte using the regression function. In some embodiments, two reporter fluorescent intensities of the reporter fluorescent dye associated with two events of the plurality of events indicate quantities of two analytes of a plurality of analytes. Two different clustering fluorescent intensities of the clustering fluorescent dye associated with the two events of the plurality of events can identify the two analytes of the plurality of analytes.

In some embodiments, each of the plurality of events is associated with a combination of clustering fluorescent intensities of at least two clustering fluorescent dyes associated with the bead in the CBA event data. Two different combinations of clustering fluorescent intensities of the at least two clustering fluorescent dyes associated with the two events of the plurality of events can identify the two analytes of the plurality of analytes.

In some embodiments, the method comprises: displaying visual indications corresponding to one or more steps of the method. The method can comprise: displaying a highlighted visual indication when performing the corresponding step of the method. In some embodiments, the method comprises: receiving a user selection of a software program module capable of performing one or more steps of the method.

In some embodiments, the method can comprise: generating output files of the plot and the table. In some embodiments, the method comprises: associating the beads and the reporter antibodies with the plurality of analytes.

Disclosed herein include embodiments of a computing system for cytometric bead array analysis. In some embodiments, the system comprises: non-transitory memory configured to store executable instructions; and a processor in communication with the non-transitory memory, the processor programmed by the executable instructions to: receive cytometric bead array (CBA) event data of a plurality of events corresponding to a plurality of samples and a plurality of standards, wherein each of the plurality of events is associated with (1) a reporter fluorescent intensity of a reporter fluorescent dye associated with a reporter antibody, (2) a clustering fluorescent intensity of a clustering fluorescent dye associated with a bead in the CBA event data. The processor is programmed by the executable instructions to: receive user selections of the reporter fluorescent dye and the clustering fluorescent dye. The processor is programmed by the executable instructions to: determine a first plurality of gates for CBA event data, based on the clustering fluorescent intensity of each of the plurality of events, to determine events of interest and corresponding analytes. The processor is programmed by the executable instructions to: receive user inputs of an initial concentration and a dilution factor of each of the plurality of analytes. The processor is programmed by the executable instructions to: receive a user selection of a regression function of a plurality of regression functions. The processor is programmed by the executable instructions to: for each of the plurality of analytes, determine a standard curve of correspondence of reporter fluorescent intensities and concentrations of the analyte using the initial concentration, the dilution factor, the regression function, and the reporter fluorescent intensities corresponding to the analyte in standard CBA event data of the CBA event data corresponding to the plurality of standards. The processor is programmed by the executable instructions to: for each sample of a plurality of samples, determine a sample concentration of each of a plurality of analytes based on the reporter fluorescent intensity in the CBA event data corresponding to the analyte using the regression function. The processor is programmed by the executable instructions to: generate (1) for each analyte of the plurality of analytes, a plot of the standard curve and the correspondence of the reporter fluorescent intensities and the concentrations of the analyte, and (2) a table comprising a sample concentration of each of the plurality of analytes for each of the plurality of samples.

In some embodiments, the computing system comprises: non-transitory memory configured to store executable instructions; and a processor in communication with the non-transitory memory, the processor programmed by the executable instructions to: receive cytometric bead array (CBA) event data of a plurality of events corresponding to a plurality of samples and a plurality of standards, wherein each of the plurality of events is associated with (1) a reporter fluorescent intensity of a reporter fluorescent dye associated with a reporter antibody, (2) a clustering fluorescent intensity of a clustering fluorescent dye associated with a bead in the CBA event data; determine a first plurality of gates for CBA event data, based on the clustering fluorescent intensity of each of the plurality of events, to determine events of interest and corresponding analytes; receive a user selection of a regression function of a plurality of regression functions; for each of the plurality of analytes, determine a standard curve of correspondence of reporter fluorescent intensities and concentrations of the analyte using the initial concentration, the dilution factor, the regression function, and the reporter fluorescent intensities corresponding to the analyte in standard CBA event data of the CBA event data corresponding to the plurality of standards; for each sample of a plurality of samples, determine a sample concentration of each of a plurality of analytes based on the reporter fluorescent intensity in sample CBA event data of the CBA event data corresponding to the analyte using the regression function; and/or generate (1) for each analyte of the plurality of analytes, a plot of the standard curve and the correspondence of the reporter fluorescent intensities and the concentrations of the analyte, and (2) a table comprising a sample concentration of each of the plurality of analytes for each of the plurality of samples.

In some embodiments, a sample of the plurality of samples comprises the plurality of analytes each at a sample concentration. A standard of the plurality of standards can comprise each of the plurality of analytes each at a standard concentration. Two standards of the plurality of standards can comprise two different standard concentrations of each of the plurality of analytes.

In some embodiments, the processor is programmed by the executable instructions to: request a user selection of a CBA assay of a plurality of CBA assays for determining the quantities of the plurality analytes or a user input of the plurality analytes. The processor can be programmed by the executable instructions to: receive the user selection of the CBA assay of the plurality of CBA assays for determining the quantities of the plurality analytes. The processor can be programmed by the executable instructions to: receive the user input of the plurality analytes.

In some embodiments, the processor is programmed by the executable instructions to: receive user selections of the standard CBA event data of the CBA event data corresponding to the plurality of standards. The processor can be programmed by the executable instructions to: receive user selections of the sample CBA event data of the CBA event data corresponding to the plurality of samples and the standard CBA event data of the CBA event data corresponding to the plurality of standards.

In some embodiments, each of the plurality of events is associated with (3) a forward scatter value, and (4) a side scatter value in the CBA event data. The processor can be programmed by the executable instructions to: determine a second plurality of gates for CBA event data, based on the forward scatter value and the side scatter value of each of the plurality of events, to determine the events of interest.

In some embodiments, the bead is associated with a clustering antibody capable of binding to an analyte of the plurality of analytes. Two beads of the beads can comprise different (1) quantities of the clustering fluorescent dye that identify the two beads and (2) clustering antibodies capable of binding to two different analytes of the plurality of analytes.

In some embodiments, to determine the standard curve, the processor is programmed by the executable instructions to: determine the standard curve of correspondence of the reporter fluorescent intensities and the concentrations of the analyte using the initial concentration, the dilution factor, the regression function, and median reporter fluorescent intensities corresponding to the analyte at different standard concentrations in the standard CBA event data of the CBA event data corresponding to the plurality of standards.

In some embodiments, to determine the sample concentration, the processor is programmed by the executable instructions to: determine the sample concentration of each of a plurality of analytes based on a median reporter fluorescent intensity in the CBA event data corresponding to the analyte using the regression function. Two reporter fluorescent intensities of the reporter fluorescent dye associated with two events of the plurality of events can indicate quantities of two analytes of a plurality of analytes. Two different clustering fluorescent intensities of the clustering fluorescent dye associated with the two events of the plurality of events can identify the two analytes of the plurality of analytes.

In some embodiments, each of the plurality of events is associated with a combination of clustering fluorescent intensities of at least two clustering fluorescent dyes associated with the bead in the CBA event data, and wherein two different combinations of clustering fluorescent intensities of the at least two clustering fluorescent dyes associated with the two events of the plurality of events identify the two analytes of the plurality of analytes.

In some embodiments, the processor is programmed by the executable instructions to: display visual indications corresponding to one or more steps performed by the processor. The processor can be programmed by the executable instructions to: highlight a visual indication when performing the corresponding step. In some embodiments, the processor is programmed by the executable instructions to: receive a user selection of a software program module capable of performing one or more steps performed by the processor.

In some embodiments, the processor is programmed by the executable instructions to: generate output files of the plot and the table. In some embodiments, the CBA event data is generated after associating the beads and the reporter antibodies with the plurality of analytes.

Disclosed herein include embodiments of a computer readable medium storing executable instructions that when executed, cause a processor (e.g., a hardware processor or a virtual processor) to perform: receiving cytometric bead array (CBA) event data of a plurality of events corresponding to a plurality of samples and a plurality of standards. Each of the plurality of events can be associated with (1) a reporter fluorescent intensity of a reporter fluorescent dye associated with a reporter antibody, and (2) a clustering fluorescent intensity of a clustering fluorescent dye associated with a bead in the CBA event data. The executable instructions when executed can cause the processor to perform: receiving user selections of the reporter fluorescent dye and the clustering fluorescent dye. Thee executable instructions when executed can cause the processor to perform: determining a first plurality of gates for CBA event data, based on the clustering fluorescent intensity of each of the plurality of events, to determine events of interest and corresponding analytes. The executable instructions when executed can cause the processor to perform: receiving user inputs of an initial concentration and a dilution factor of each of the plurality of analytes. The executable instructions when executed can cause the processor to perform: receiving a user selection of a regression function of a plurality of regression functions. The executable instructions when executed can cause the processor to perform: for each of the plurality of analytes, determining a standard curve of correspondence of reporter fluorescent intensities and concentrations of the analyte using the initial concentration, the dilution factor, the regression function, and the reporter fluorescent intensities corresponding to the analyte in standard CBA event data of the CBA event data corresponding to the plurality of standards. The executable instructions when executed can cause the processor to perform: for each sample of a plurality of samples, determining a sample concentration of each of a plurality of analytes based on the reporter fluorescent intensity in sample CBA event data of the CBA event data corresponding to the analyte using the regression function. The executable instructions when executed can cause the processor to perform: generating (1) for each analyte of the plurality of analytes, a plot of the standard curve and the correspondence of the reporter fluorescent intensities and the concentrations of the analyte, and/or (2) a table comprising a sample concentration of each of the plurality of analytes for each of the plurality of samples.

In some embodiments, the computer readable medium stores executable instructions that when executed, cause a processor (e.g., a hardware processor or a virtual processor) to perform: receiving cytometric bead array (CBA) event data of a plurality of events corresponding to a plurality of samples and a plurality of standards, wherein each of the plurality of events is associated with (1) a reporter fluorescent intensity of a reporter fluorescent dye associated with a reporter antibody, and (2) a clustering fluorescent intensity of a clustering fluorescent dye associated with a bead in the CBA event data, wherein the plurality of standards is associated with an initial concentration and a dilution factor of each of the plurality of analytes; determining a first plurality of gates for CBA event data, based on the clustering fluorescent intensity of each of the plurality of events, to determine events of interest and corresponding analytes of the plurality of analytes; receiving a user selection of a regression function of a plurality of regression functions; for each of the plurality of analytes, determining a standard curve of correspondence of reporter fluorescent intensities and concentrations of the analyte using the initial concentration, the dilution factor, the regression function, and the reporter fluorescent intensities corresponding to the analyte in standard CBA event data of the CBA event data corresponding to the plurality of standards; for each sample of a plurality of samples, determining a sample concentration of each of a plurality of analytes based on the reporter fluorescent intensity in sample CBA event data of the CBA event data corresponding to the analyte using the regression function; and/or generating (1) for each analyte of the plurality of analytes, a plot of the standard curve and the correspondence of the reporter fluorescent intensities and the concentrations of the analyte, and (2) a table comprising a sample concentration of each of the plurality of analytes for each of the plurality of samples.

In some embodiments, a sample of the plurality of samples comprises the plurality of analytes each at a sample concentration. A standard of the plurality of standards can comprise each of the plurality of analytes each at a standard concentration. Two standards of the plurality of standards can comprise two different standard concentrations of each of the plurality of analytes.

In some embodiments, the executable instructions when executed can cause the processor to perform: requesting a user selection of a CBA assay of a plurality of CBA assays for determining the quantities of the plurality analytes or a user input of the plurality of analytes. The executable instructions when executed can cause the processor to perform: receiving the user selection of the CBA assay of the plurality of CBA assays for determining the quantities of the plurality analytes. The executable instructions when executed can cause the processor to perform: receiving the user input of the plurality analytes.

In some embodiments, the executable instructions when executed can cause the processor to perform: receiving user selections of the standard CBA event data of the CBA event data corresponding to the plurality of standards. The executable instructions when executed can cause the processor to perform: receiving user selections of the sample CBA event data of the CBA event data corresponding to the plurality of samples and the standard CBA event data of the CBA event data corresponding to the plurality of standards.

In some embodiments, each of the plurality of events is associated with (3) a forward scatter value, and (4) a side scatter value in the CBA event data. The executable instructions when executed can cause the processor to perform: determining a second plurality of gates for the CBA event data, based on the forward scatter value and the side scatter value of each of the plurality of events, to determine the events of interest.

In some embodiments, the bead is associated with a clustering antibody capable of binding to an analyte of the plurality of analytes. Two beads of the beads can comprise different (1) quantities of the clustering fluorescent dye that identify the two beads and (2) clustering antibodies capable of binding to two different analytes of the plurality of analytes.

In some embodiments, determining the standard curve comprises: determining the standard curve of correspondence of the reporter fluorescent intensities and the concentrations of the analyte using the initial concentration, the dilution factor, the regression function, and median reporter fluorescent intensities corresponding to the analyte at different standard concentrations in the standard CBA event data of the CBA event data corresponding to the plurality of standards.

In some embodiments, determining the sample concentration comprises determining the sample concentration of each of a plurality of analytes based on a median reporter fluorescent intensity in the CBA event data corresponding to the analyte using the regression function. In some embodiments, two reporter fluorescent intensities of the reporter fluorescent dye associated with two events of the plurality of events indicate quantities of two analytes of a plurality of analytes. Two different clustering fluorescent intensities of the clustering fluorescent dye associated with the two events of the plurality of events can identify the two analytes of the plurality of analytes.

In some embodiments, each of the plurality of events is associated with a combination of clustering fluorescent intensities of at least two clustering fluorescent dyes associated with the bead in the CBA event data. Two different combinations of clustering fluorescent intensities of the at least two clustering fluorescent dyes associated with the two events of the plurality of events can identify the two analytes of the plurality of analytes.

In some embodiments, the method comprises: displaying visual indications corresponding to one or more steps performed by the processor. The method can comprise: displaying a highlighted visual indication when performing the corresponding step. In some embodiments, the method comprises: receiving a user selection of a software program module capable of performing one or more steps performed by the processor.

In some embodiments, the method can comprise: generating output files of the plot and the table. In some embodiments, the method comprises: associating the beads and the reporter antibodies with the plurality of analytes.

BRIEF DESCRIPTION OF THE DRAWINGS

Figure 6B:
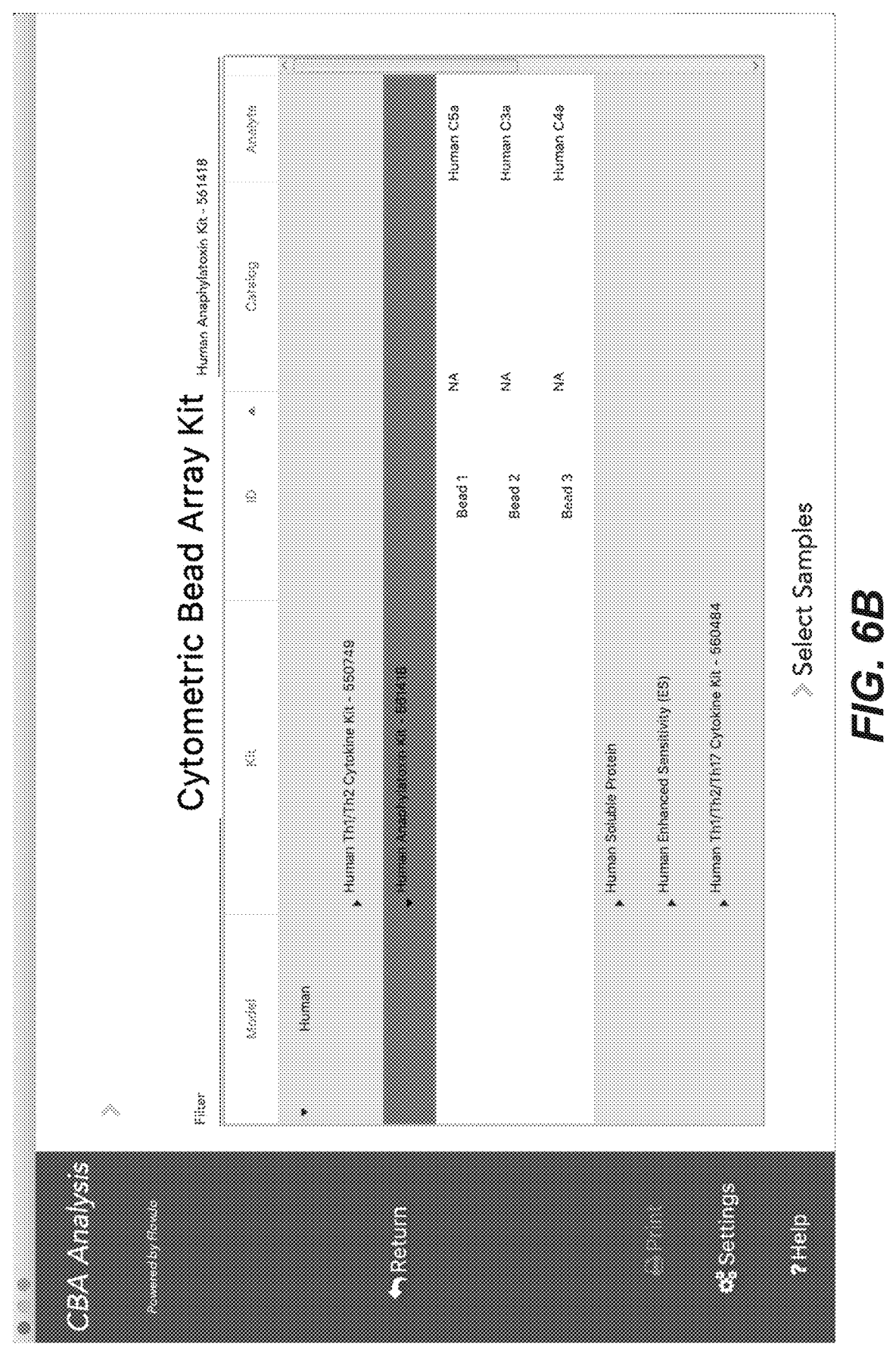

FIG. 6A, 6B, 6C, 6D, 6E, 6F, 6G, 6H, and 6I are each a non-limiting exemplary illustration of a user interface design for performing bead array analysis.

Figure 7C:
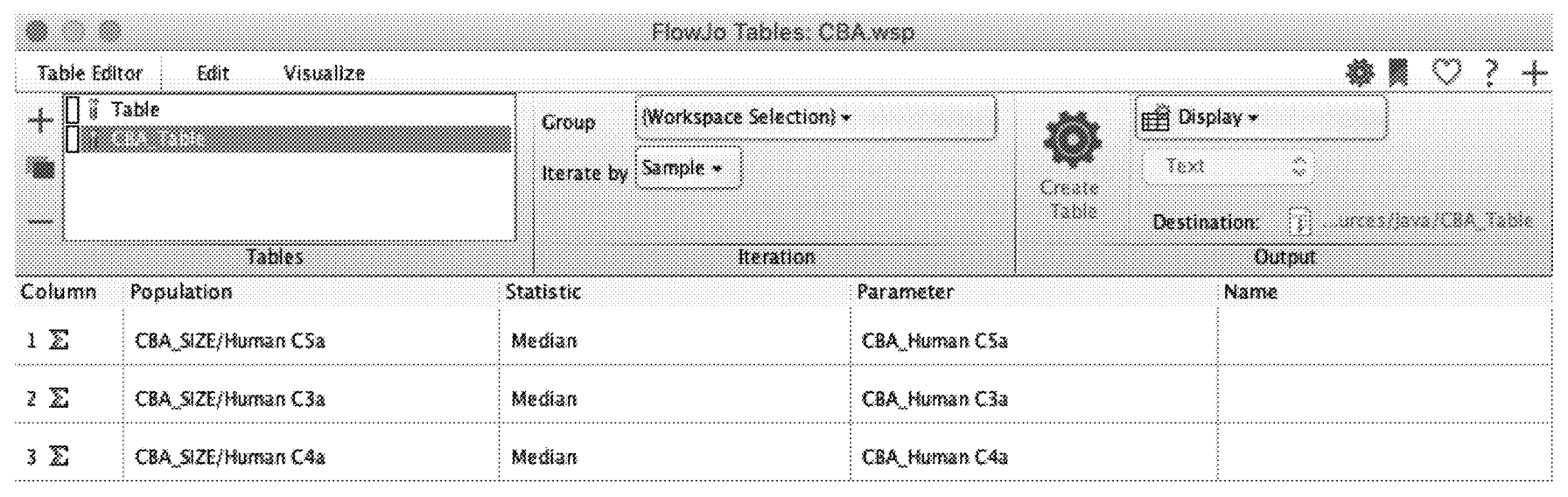

FIG. 7A, 7B, 7C, 7D, and 7E are each a non-limiting exemplary illustration of a user interface design for outputting the result of bead array analysis.

Figure 10B:
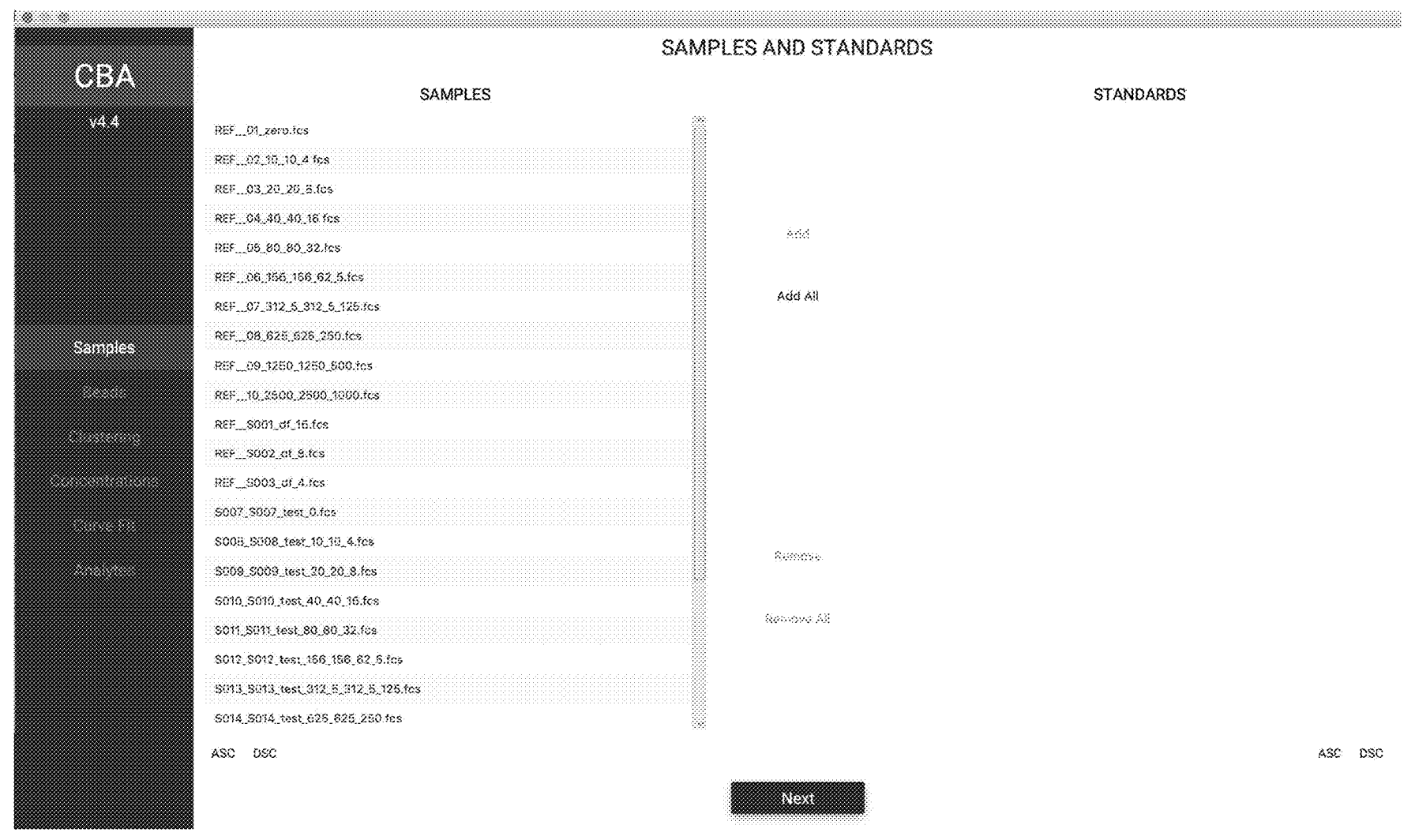

FIG. 10A, 10B, 10C, 10D, 10E, and 10F are each a non-limiting exemplary illustration of a user interface design for performing bead array analysis.

FIG. 11A, 11B, 11C, 11D, and 11E are each a non-limiting exemplary illustration of a user interface design for outputting the result of bead array analysis.

DETAILED DESCRIPTION

Figure 1:
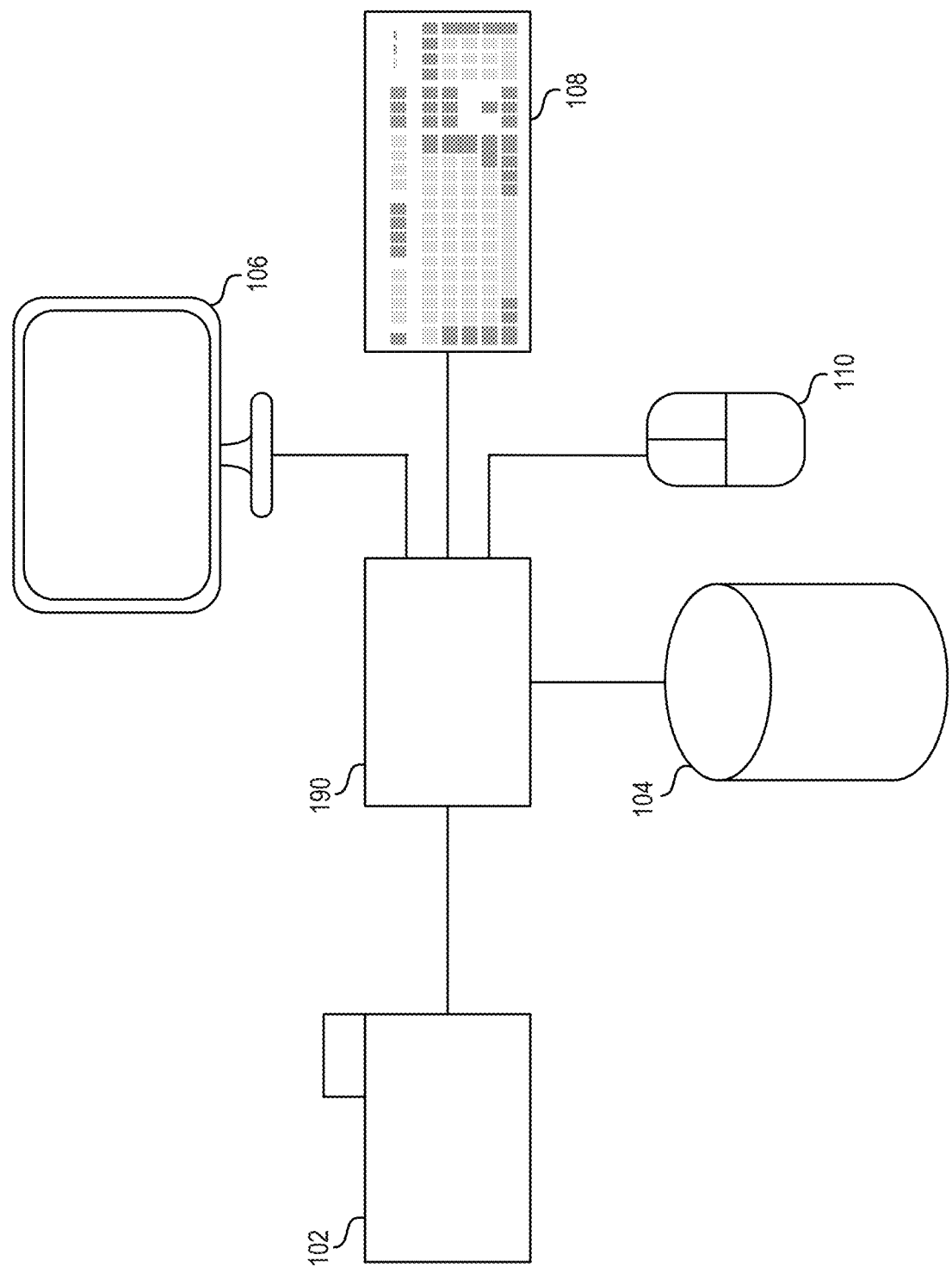
FIG. 1 shows a functional block diagram for one example of a sorting control system for analyzing and displaying biological events.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments can be utilized, and other changes can be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

Particle analyzers, such as flow and scanning cytometers, are analytical tools that enable the characterization of particles on the basis of electro-optical measurements such as light scatter and fluorescence. In a flow cytometer, for example, particles, such as molecules, analyte-bound beads, or individual cells, in a fluid suspension are passed by a detection region in which the particles are exposed to an excitation light, typically from one or more lasers, and the light scattering and fluorescence properties of the particles are measured. Particles or components thereof typically are labeled with fluorescent dyes to facilitate detection. A multiplicity of different particles or components can be simultaneously detected by using spectrally distinct fluorescent dyes to label the different particles or components. In some implementations, a multiplicity of photodetectors, one for each of the scatter parameters to be measured, and one or more for each of the distinct dyes to be detected are included in the analyzer. For example, some embodiments include spectral configurations where more than one sensor or detector is used per dye. The data obtained comprise the signals measured for each of the light scatter detectors and the fluorescence emissions.

Particle analyzers can further comprise means for recording the measured data and analyzing the data. For example, data storage and analysis can be carried out using a computer connected to the detection electronics. For example, the data can be stored in tabular form, where each row corresponds to data for one particle, and the columns correspond to each of the measured features. The use of standard file formats, such as a Flow Cytometry Standard ("FCS") file format, for storing data from a particle analyzer facilitates analyzing data using separate programs and/or machines. Using current analysis methods, the data typically are displayed in 1-dimensional histograms or 2-dimensional (2D) plots for ease of visualization, but other methods can be used to visualize multidimensional data.

The parameters measured using, for example, a flow cytometer typically include light scattered by the particle in a narrow angle along a mostly forward direction (referred to as forward scatter (FSC)), light that is scattered by the particle in an orthogonal direction to the excitation laser (referred to as side scatter (SSC)), and the light emitted from fluorescent molecules in one or more detectors that measure signal over a range of spectral wavelengths, or by the fluorescent dye that is primarily detected in that specific detector or array of detectors. Different cell types can be identified by their light scatter characteristics and fluorescence emissions resulting from labeling various cell proteins or other constituents with fluorescent dye-labeled antibodies or other fluorescent probes.

Both flow and scanning cytometers are commercially available from, for example, BD Biosciences (San Jose, Calif.). Flow cytometry is described in, for example, Landy et al. (eds.), Clinical Flow Cytometry, Annals of the New York Academy of Sciences Volume 677 (1993); Bauer et al. (eds.), Clinical Flow Cytometry: Principles and Applications, Williams & Wilkins (1993); Ormerod (ed.), Flow Cytometry: A Practical Approach, Oxford Univ. Press (1994); Jaroszeski et al. (eds.), Flow Cytometry Protocols, Methods in Molecular Biology No. 91, Humana Press (1997); and Practical Shapiro, Flow Cytometry, 4th ed., Wiley-Liss (2003); each of which is incorporated herein by reference. Fluorescence imaging microscopy is described in, for example, Pawley (ed.), Handbook of Biological Confocal Microscopy, 2nd Edition, Plenum Press (1989), incorporated herein by reference.

The data obtained from an analysis of cells (or other particles) by multi-color flow cytometry are multidimensional, where each cell corresponds to a point in a multidimensional space defined by the parameters measured. Populations of cells or particles can be identified as clusters of points in the data space. The identification of clusters and, thereby, populations can be carried out manually by drawing a gate around a population displayed in one or more 2-dimensional plots, referred to as "scatter plots" or "dot plots," of the data. Alternatively, clusters can be identified, and gates that define the limits of the populations, can be determined automatically. Examples of methods for automated gating have been described in, for example, U.S. Pat. Nos. 4,845,653; 5,627,040; 5,739,000; 5,795,727; 5,962,238; 6,014,904; 6,944,338; and 8,990,047; each of which is incorporated herein by reference.

Flow cytometry is a valuable method for the analysis and isolation of biological particles such as cells and constituent molecules. As such it has a wide range of diagnostic and therapeutic applications. The method utilizes a fluid stream to linearly segregate particles such that they can pass, single file, through a detection apparatus. Individual cells can be distinguished according to their location in the fluid stream and the presence of detectable markers. Thus, a flow cytometer can be used to characterize and produce a diagnostic profile of a population of biological particles.

Isolation of biological particles has been achieved by adding a sorting or collection capability to flow cytometers. Particles in a segregated stream, detected as having one or more desired characteristics, can be individually isolated from the sample stream by mechanical or electrical separation. This method of flow sorting has been used to sort cells of different types, to separate sperm bearing X and Y chromosomes for animal breeding, to sort chromosomes for genetic analysis, and to isolate particular organisms from complex biological population.

Gating can be used to classify and help make sense of the large quantity of data that can be generated from a sample. Given the large quantities of data presented for a given sample, there exists a need to efficiently control the graphical display of the data.

Fluorescence-activated particle sorting or cell sorting is a specialized type of flow cytometry. Fluorescence-activated particle sorting or cell sorting provides a method for sorting a heterogeneous mixture of particles into one or more containers, one cell at a time, based upon the specific light scattering and fluorescent characteristics of each cell. It records fluorescent signals from individual cells, and physically separates cells of particular interest. The acronym FACS is trademarked and owned by Becton, Dickinson and Company (Franklin Lakes, N.J.) and can be used to refer to devices for performing fluorescence-activated particle sorting or cell sorting.

The particle suspension is placed near the center of a narrow, rapidly flowing stream of liquid. The flow is arranged so that on the average there is a large separation between particles relative to their diameter as they arrive stochastically (e.g., a Poisson process) into the detection region. A vibrating mechanism can cause the emerging fluid stream to break off in a stable manner into individual droplets that contain particles previously characterized in the detection region. The system can generally be adjusted so that there is a low probability of more than one particle being in a droplet. If a particle is classified to be collected, a charge can be applied to the flow cell and emerging stream during the period of time one or more drops form and break off from the stream. These charged droplets then move through an electrostatic deflection system that diverts droplets into target containers based upon the charge applied to the droplet.

A sample can include thousands if not millions of cells. Cells can be sorted to purify a sample to the cells of interest. The sorting process can generally identify three varieties of cells: cells of interest, cells which are not of interest, and cells which cannot be identified. In order to sort cells with high purity (e.g., high concentration of cells of interest), droplet generating cell sorters can abort the sort electronically if the desired cells are too close to another unwanted cell and thereby reduce contamination of the sorted populations by any inadvertent inclusion of an unwanted particle within the droplet containing the particle of interest.

Disclosed herein include embodiments of a method for cytometric bead array analysis. In some embodiments, the method is under control of a processor (e.g., a hardware processor or a virtual processor) and comprises: receiving cytometric bead array (CBA) event data of a plurality of events corresponding to a plurality of samples and a plurality of standards. Each of the plurality of events can be associated with (1) a reporter fluorescent intensity of a reporter fluorescent dye associated with a reporter antibody, and (2) a clustering fluorescent intensity of a clustering fluorescent dye associated with a bead in the CBA event data. The method can comprise: receiving user selections of the reporter fluorescent dye and the clustering fluorescent dye. The method can comprise: determining a first plurality of gates for CBA event data, based on the clustering fluorescent intensity of each of the plurality of events, to determine events of interest and corresponding analytes. The method can comprise: receiving user inputs of an initial concentration and a dilution factor of each of the plurality of analytes. The method can comprise: receiving a user selection of a regression function of a plurality of regression functions. The method can comprise: for each of the plurality of analytes, determining a standard curve of correspondence of reporter fluorescent intensities and concentrations of the analyte using the initial concentration, the dilution factor, the regression function, and the reporter fluorescent intensities corresponding to the analyte in standard CBA event data of the CBA event data corresponding to the plurality of standards. The method can comprise: for each sample of a plurality of samples, determining a sample concentration of each of a plurality of analytes based on the reporter fluorescent intensity in sample CBA event data of the CBA event data corresponding to the analyte using the regression function. The method can comprise: generating for each analyte of the plurality of analytes, a plot of the standard curve and the correspondence of the reporter fluorescent intensities and the concentrations of the analyte, and/or (2) a table comprising a sample concentration of each of the plurality of analytes for each of the plurality of samples.

Disclosed herein include embodiments of a computing system for cytometric bead array analysis. In some embodiments, the system comprises: non-transitory memory configured to store executable instructions; and a processor in communication with the non-transitory memory, the processor programmed by the executable instructions to: receive cytometric bead array (CBA) event data of a plurality of events corresponding to a plurality of samples and a plurality of standards, wherein each of the plurality of events is associated with (1) a reporter fluorescent intensity of a reporter fluorescent dye associated with a reporter antibody, a clustering fluorescent intensity of a clustering fluorescent dye associated with a bead in the CBA event data. The processor is programmed by the executable instructions to: receive user selections of the reporter fluorescent dye and the clustering fluorescent dye. The processor is programmed by the executable instructions to: determine a first plurality of gates for CBA event data, based on the clustering fluorescent intensity of each of the plurality of events, to determine events of interest and corresponding analytes. The processor is programmed by the executable instructions to: receive user inputs of an initial concentration and a dilution factor of each of the plurality of analytes. The processor is programmed by the executable instructions to: receive a user selection of a regression function of a plurality of regression functions. The processor is programmed by the executable instructions to: for each of the plurality of analytes, determine a standard curve of correspondence of reporter fluorescent intensities and concentrations of the analyte using the initial concentration, the dilution factor, the regression function, and the reporter fluorescent intensities corresponding to the analyte in standard CBA event data of the CBA event data corresponding to the plurality of standards. The processor is programmed by the executable instructions to: for each sample of a plurality of samples, determine a sample concentration of each of a plurality of analytes based on the reporter fluorescent intensity in the CBA event data corresponding to the analyte using the regression function. The processor is programmed by the executable instructions to: generate (1) for each analyte of the plurality of analytes, a plot of the standard curve and the correspondence of the reporter fluorescent intensities and the concentrations of the analyte, and (2) a table comprising a sample concentration of each of the plurality of analytes for each of the plurality of samples.

Disclosed herein include embodiments of a computer readable medium storing executable instructions that when executed, cause a processor (e.g., a hardware processor or a virtual processor) to perform: receiving cytometric bead array (CBA) event data of a plurality of events corresponding to a plurality of samples and a plurality of standards. Each of the plurality of events can be associated with (1) a reporter fluorescent intensity of a reporter fluorescent dye associated with a reporter antibody, and (2) a clustering fluorescent intensity of a clustering fluorescent dye associated with a bead in the CBA event data. The executable instructions when executed can cause the processor to perform: receiving user selections of the reporter fluorescent dye and the clustering fluorescent dye. Thee executable instructions when executed can cause the processor to perform: determining a first plurality of gates for CBA event data, based on the clustering fluorescent intensity of each of the plurality of events, to determine events of interest and corresponding analytes. The executable instructions when executed can cause the processor to perform: receiving user inputs of an initial concentration and a dilution factor of each of the plurality of analytes. The executable instructions when executed can cause the processor to perform: receiving a user selection of a regression function of a plurality of regression functions. The executable instructions when executed can cause the processor to perform: for each of the plurality of analytes, determining a standard curve of correspondence of reporter fluorescent intensities and concentrations of the analyte using the initial concentration, the dilution factor, the regression function, and the reporter fluorescent intensities corresponding to the analyte in standard CBA event data of the CBA event data corresponding to the plurality of standards. The executable instructions when executed can cause the processor to perform: for each sample of a plurality of samples, determining a sample concentration of each of a plurality of analytes based on the reporter fluorescent intensity in sample CBA event data of the CBA event data corresponding to the analyte using the regression function. The executable instructions when executed can cause the processor to perform: generating (1) for each analyte of the plurality of analytes, a plot of the standard curve and the correspondence of the reporter fluorescent intensities and the concentrations of the analyte, and/or (2) a table comprising a sample concentration of each of the plurality of analytes for each of the plurality of samples.

Definitions

As used herein, the terms set forth with particularity below have the following definitions. If not otherwise defined in this section, all terms used herein have the meaning commonly understood by a person skilled in the arts to which this invention belongs.

As used herein, "system," "instrument," "apparatus," and "device" generally encompass both the hardware (e.g., mechanical and electronic) and, in some implementations, associated software (e.g., specialized computer programs for graphics control) components.

As used herein, an "event" or "event data" generally refers to the data (e.g., assembled packet of data) measured from a single particle, such as cells or synthetic particles. Typically, the data measured from a single particle include a number of parameters or features, including one or more light scattering parameters or features, and at least one other parameter or feature derived from fluorescence detected from the particle such as the intensity of the fluorescence. Thus, each event can be represented as a vector of parameter and feature measurements, wherein each measured parameter or feature corresponds to one dimension of the data space. In some embodiments, the data measured from a single particle include image, electric, temporal, or acoustic data. An event can be associated with an experiment, an assay, or a sample source which can be identified in association with the measurement data.

As used herein, a "population", or "subpopulation" of particles, such as cells or other particles, generally refers to a group of particles that possess properties (for example, optical, impedance, or temporal properties) with respect to one or more measured parameters such that measured parameter data form a cluster in the data space. Thus, populations can be recognized as clusters in the data. Conversely, each data cluster generally is interpreted as corresponding to a population of a particular type of cell or particle, although clusters that correspond to noise or background typically also are observed. A cluster can be defined in a subset of the dimensions, e.g., with respect to a subset of the measured parameters, which corresponds to populations that differ in only a subset of the measured parameters or features extracted from the measurements of the cell or particle.

As used herein, a "gate" generally refers to a classifier boundary identifying a subset of data of interest. In cytometry, a gate can bound a group of events of particular interest. As used herein, "gating" generally refers to the process of classifying the data using a defined gate for a given set of data, where the gate can be one or more regions of interest combined with Boolean logic.

Specific examples of various embodiments and systems in which they are implemented are described further below.

Sorting Control System

FIG. 1 shows a functional block diagram for one example of a sorting control system, such as an analytics controller 100, for analyzing and displaying biological events. An analytics controller 100 can be configured to implement a variety of processes for controlling graphic display of biological events.

A particle analyzer or sorting system 102 can be configured to acquire biological event data. For example, a flow cytometer can generate flow cytometric event data. The particle analyzer 102 can be configured to provide biological event data to the analytics controller 100. A data communication channel can be included between the particle analyzer 102 and the analytics controller 100. The biological event data can be provided to the analytics controller 100 via the data communication channel.

The analytics controller 100 can be configured to receive biological event data from the particle analyzer 102. The biological event data received from the particle analyzer 102 can include flow cytometric event data. The analytics controller 100 can be configured to provide a graphical display including a reporter plot of biological event data to a display device 106. The analytics controller 100 can be further configured to render a region of interest as a gate around a population of biological event data shown by the display device 106, overlaid upon the reporter plot, for example. In some embodiments, the gate can be a logical combination of one or more graphical regions of interest drawn upon a single parameter histogram or bivariate plot.

The analytics controller 100 can be further configured to display the biological event data on the display device 106 within the gate differently from other events in the biological event data outside of the gate. For example, the analytics controller 100 can be configured to render the color of biological event data contained within the gate to be distinct from the color of biological event data outside of the gate. The display device 106 can be implemented as a monitor, a tablet computer, a smartphone, or other electronic device configured to present graphical interfaces.

The analytics controller 100 can be configured to receive a gate selection signal identifying the gate from a reporter input device. For example, the reporter input device can be implemented as a mouse 110. The mouse 110 can initiate a gate selection signal to the analytics controller 100 identifying the gate to be displayed on or manipulated via the display device 106 (e.g., by clicking on or in the desired gate when the cursor is positioned there). In some implementations, the reporter device can be implemented as the keyboard 108 or other means for providing an input signal to the analytics controller 100 such as a touchscreen, a stylus, an optical detector, or a voice recognition system. Some input devices can include multiple inputting functions. In such implementations, the inputting functions can each be considered an input device. For example, as shown in FIG. 1, the mouse 110 can include a right mouse button and a left mouse button, each of which can generate a triggering event.

The triggering event can cause the analytics controller 100 to alter the manner in which the data is displayed, which portions of the data is actually displayed on the display device 106, and/or provide input to further processing such as selection of a population of interest for particle sorting.

In some embodiments, the analytics controller 100 can be configured to detect when gate selection is initiated by the mouse 110. The analytics controller 100 can be further configured to automatically modify plot visualization to facilitate the gating process. The modification can be based on the specific distribution of biological event data received by the analytics controller 100.

The analytics controller 100 can be connected to a storage device 104. The storage device 104 can be configured to receive and store biological event data from the analytics controller 100. The storage device 104 can also be configured to receive and store flow cytometric event data from the analytics controller 100. The storage device 104 can be further configured to allow retrieval of biological event data, such as flow cytometric event data, by the analytics controller 100.

A display device 106 can be configured to receive display data from the analytics controller 100. The display data can comprise plots of biological event data and gates outlining sections of the plots. The display device 106 can be further configured to alter the information presented according to input received from the analytics controller 100 in conjunction with input from the particle analyzer 102, the storage device 104, the keyboard 108, and/or the mouse 110.

In some implementations the analytics controller 100 can generate a user interface to receive example events for sorting. For example, the user interface can include a control for receiving example events or example images. The example events or images or an example gate can be provided prior to collection of event data for a sample, or based on an initial set of events for a portion of the sample.
Particle Sorter System A common flow sorting technique which can be referred to as "electrostatic cell sorting," utilizes droplet sorting in which a stream or moving fluid column containing linearly segregated particles is broken into drops and the drops containing particles of interest are electrically charged and deflected into a collection tube by passage through an electric field. Droplet sorting systems are capable of forming drops at a rate of 100,000 drops/clustering in a fluid stream that is passed through a nozzle having a diameter less than 100 micrometers. Droplet sorting typically requires that the drops break off from the stream at a fixed distance from the nozzle tip. The distance is normally on the order of a few millimeters from the nozzle tip and can be stabilized and maintained for an unperturbed fluid stream by oscillating the nozzle tip at a predefined frequency with an amplitude to hold the break-off constant. For example, in some embodiments, adjusting amplitude of a sine wave shaped voltage pulse at a given frequency holds the break-off stable and constant.

Typically, the linearly entrained particles in the stream are characterized as they pass through an observation point situated within a flow cell or cuvette, or just below the nozzle tip. Once a particle is identified as meeting one or more desired criteria, the time at which it will reach the drop break-off point and break from the stream in a drop can be predicted. Ideally, a brief charge is applied to the fluid stream just before the drop containing the selected particle breaks from the stream and then grounded immediately after the drop breaks off. The drop to be sorted maintains an electrical charge as it breaks off from the fluid stream, and all other drops are left uncharged. The charged drop is deflected sideways from the downward trajectory of the other drops by an electrical field and collected in a sample tube. The uncharged drops fall directly into a drain.

Figure 2A:
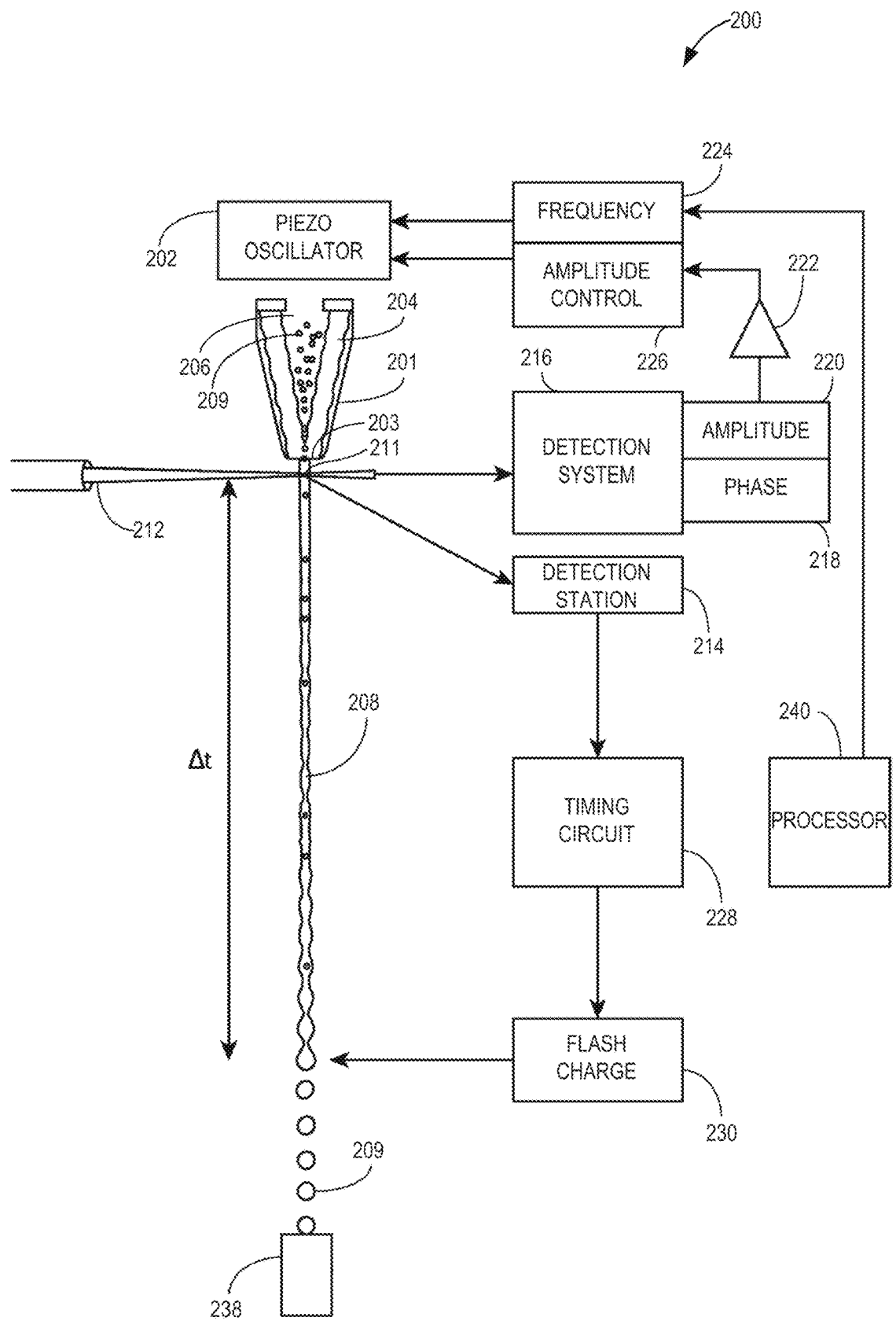
FIG. 2A is a schematic drawing of a particle sorter system, in accordance with one embodiment presented herein.

FIG. 2A is a schematic drawing of a particle sorter system 200 (e.g., the particle analyzer 102) in accordance with one embodiment presented herein. In some embodiments, the particle sorter system 200 is a cell sorter system. As shown in FIG. 2A, a drop formation transducer 202 (e.g., piezo-oscillator) is coupled to a fluid conduit 201, which can be coupled to, can include, or can be, a nozzle 203. Within the fluid conduit 201, sheath fluid 204 hydrodynamically focuses a sample fluid 206 comprising particles 209 into a moving fluid column 208 (e.g. a stream). Within the moving fluid column 208, particles 209 (e.g., cells) are lined up in single file to cross a monitored area 211 (e.g., where laser-stream intersect), irradiated by an irradiation source 212 (e.g., a laser). Vibration of the drop formation transducer 202 causes moving fluid column 208 to break into a plurality of drops 210, some of which contain particles 209.

In operation, a detection station 214 (e.g., an event detector) identifies when a particle of interest (or cell of interest) crosses the monitored area 211. Detection station 214 feeds into a timing circuit 228, which in turn feeds into a flash charge circuit 230. At a drop break off point, informed by a timed drop delay (Δt), a flash charge can be applied to the moving fluid column 208 such that a drop of interest carries a charge. The drop of interest can include one or more particles or cells to be sorted. The charged drop can then be sorted by activating deflection plates (not shown) to deflect the drop into a vessel such as a collection tube or a multi-well or microwell sample plate where a well or microwell can be associated with drops of particular interest. As shown in FIG. 2A, the drops can be collected in a drain receptacle 238.

A detection system 216 (e.g. a drop boundary detector) serves to automatically determine the phase of a drop drive signal when a particle of interest passes the monitored area 211. An exemplary drop boundary detector is described in U.S. Pat. No. 7,679,039, which is incorporated herein by reference in its entirety. The detection system 216 allows the instrument to accurately calculate the place of each detected particle in a drop. The detection system 216 can feed into an amplitude signal 220 and/or phase 218 signal, which in turn feeds (via amplifier 222) into an amplitude control circuit 226 and/or frequency control circuit 224. The amplitude control circuit 226 and/or frequency control circuit 224, in turn, controls the drop formation transducer 202. The amplitude control circuit 226 and/or frequency control circuit 224 can be included in a control system.

In some implementations, sort electronics (e.g., the detection system 216, the detection station 214 and a processor 240) can be coupled with a memory configured to store the detected events and a sort decision based thereon. The sort decision can be included in the event data for a particle. In some implementations, the detection system 216 and the detection station 214 can be implemented as a single detection unit or communicatively coupled such that an event measurement can be collected by one of the detection system 216 or the detection station 214 and provided to the non-collecting element.

Figure 2B:
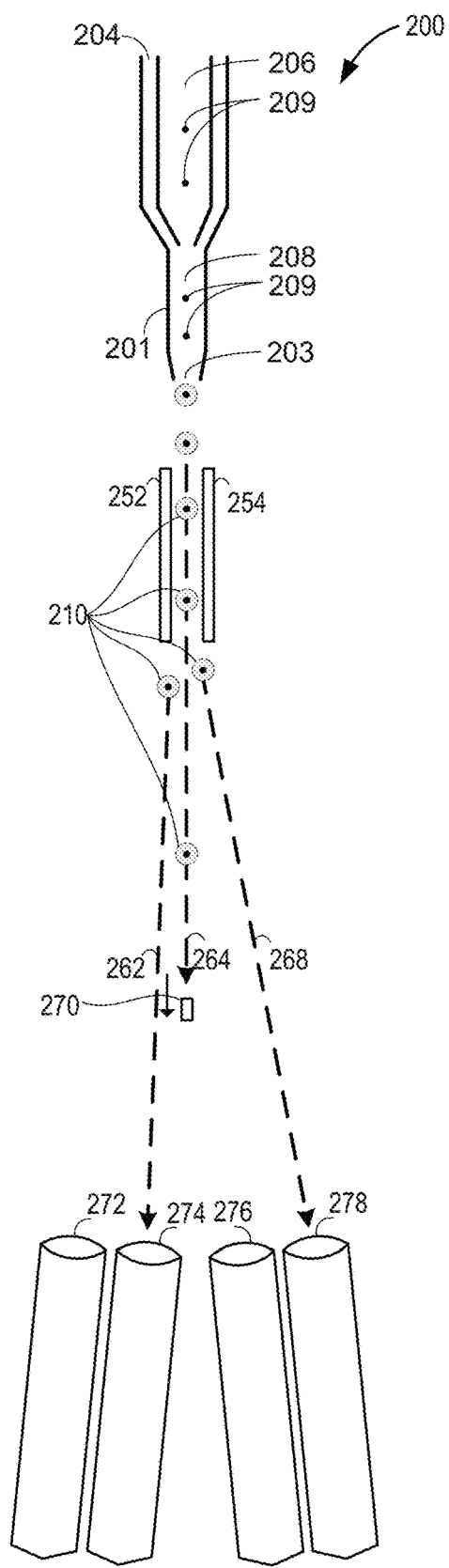
FIG. 2B is a schematic drawing of another particle sorter system, in accordance with one embodiment presented herein.

FIG. 2B is a schematic drawing of a particle sorter system, in accordance with one embodiment presented herein. The particle sorter system 200 shown in FIG. 2B, includes deflection plates 252 and 254. A charge can be applied via a stream-charging wire in a barb. This creates a stream of droplets 210 containing particles 210 for analysis. The particles can be illuminated with one or more light sources (e.g., lasers) to generate light scatter and fluorescence information. The information for a particle is analyzed such as by sorting electronics or other detection system (not shown in FIG. 2B). The deflection plates 252 and 254 can be independently controlled to attract or repel the charged droplet to guide the droplet toward a destination collection receptacle (e.g., one of 272, 274, 276, or 278). As shown in FIG. 2B, the deflection plates 252 and 254 can be controlled to direct a particle along a reporter path 262 toward the receptacle 274 or along a clustering path 268 toward the receptacle 278. If the particle is not of interest (e.g., does not exhibit scatter or illumination information within a specified sort range), deflection plates may allow the particle to continue along a flow path 264. Such uncharged droplets may pass into a waste receptacle such as via aspirator 270.

The sorting electronics can be included to initiate collection of measurements, receive fluorescence signals for particles, and determine how to adjust the deflection plates to cause sorting of the particles. Example implementations of the embodiment shown in FIG. 2B include the BD FACSAria™ line of flow cytometers commercially provided by Becton, Dickinson and Company (Franklin Lakes, N.J.).

In some embodiments, one or more components described for the particle sorter system 200 can be used to analyze and characterize particles, with or without physically sorting the particles into collection vessels. Likewise, one or more components described below for the particle analysis system 300 (FIG. 3) can be used to analyze and characterize particles, with or without physically sorting the particles into collection vessels. For example, particles can be grouped or displayed in a tree that includes at least three groups as described herein, using one or more of the components of the particle sorter system 200 or particle analysis system 300.

Figure 3:
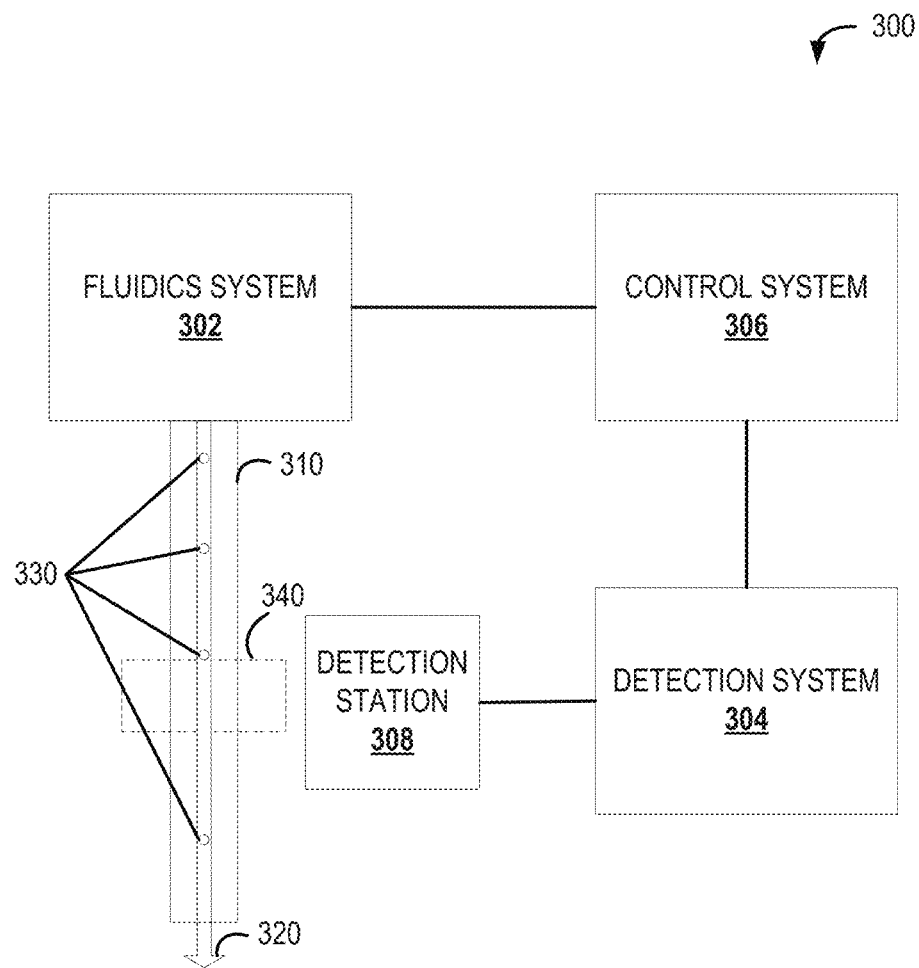
FIG. 3 shows a functional block diagram of a particle analysis system for computational based sample analysis and particle characterization.

FIG. 3 shows a functional block diagram of a particle analysis system for computational based sample analysis and particle characterization. In some embodiments, the particle analysis system 300 is a flow system. The particle analysis system 300 shown in FIG. 3 can be configured to perform, in whole or in part, the methods described herein such as. The particle analysis system 300 includes a fluidics system 302. The fluidics system 302 can include or be coupled with a sample tube 310 and a moving fluid column within the sample tube in which particles 330 (e.g. cells) of a sample move along a common sample path 320.

The particle analysis system 300 includes a detection system 304 configured to collect a signal from each particle as it passes one or more detection stations along the common sample path. A detection station 308 generally refers to a monitored area 340 of the common sample path. Detection can, in some implementations, include detecting light or one or more other properties of the particles 330 as they pass through a monitored area 340. In FIG. 3, one detection station 308 with one monitored area 340 is shown. Some implementations of the particle analysis system 300 can include multiple detection stations. Furthermore, some detection stations can monitor more than one area.

Each signal is assigned a signal value to form a data point for each particle. As described above, this data can be referred to as event data. The data point can be a multidimensional data point including values for respective properties measured for a particle. The detection system 304 is configured to collect a succession of such data points in a reporter time interval.

The particle analysis system 300 can also include a control system 306. The control system 306 can include one or more processors, an amplitude control circuit 226 and/or a frequency control circuit 224 as shown in FIG. 2B. The control system 206 shown can be operationally associated with the fluidics system 302. The control system 206 can be configured to generate a calculated signal frequency for at least a portion of the reporter time interval based on a Poisson distribution and the number of data points collected by the detection system 304 during the reporter time interval. The control system 306 can be further configured to generate an experimental signal frequency based on the number of data points in the portion of the reporter time interval. The control system 306 can additionally compare the experimental signal frequency with that of a calculated signal frequency or a predetermined signal frequency.

Bead-Based Immunoassays and Analysis

Flow cytometers can be used for the characterization of particles on the basis of light scatter and fluorescence. In a flow cytometer, particles can be individually analyzed by exposing each particle to an excitation light, typically one or more lasers, and the light scattering and fluorescence properties of the particles are measured. Particles, such as molecules, analyte-bound beads, individual cells, or subcomponents thereof, can be labeled with one or more spectrally distinct fluorescent dyes or fluorophores, and detection can be carried out using a multiplicity of photodetectors, one for each distinct dye to be detected.

Beads, Capture Reagents, and Reporter Reagents. Microparticles (e.g., beads) coated with one member of a binding pair (e.g., a capture reagent and a reporter reagent) can be used for an analyte quantification assay (e.g., a bead-based immunoassay, such as the BD™ (Franklin Lakes, N.J.) Cytometric Bead Array, LEGENDplex™ from BioLegend (San Diego, Calif.). For example, beads (e.g., cytometric beads) of all bead populations can be labeled with the same flourescent dye, and beads of different bead populations can be labeled with different quantities of the fluorescent dye. The identities of the beads of different bead populations can be determined based on the fluorescent intensities of the beads from the fluorescent dye after excitation by light (e.g., laser light). As another example, beads of all bead populations can be labeled with two (or more) flourescent dyes, and beads of different bead populations can be labeled with different quantities of each of the two (or more) fluorescent dyes. The identities of the beads of different bead populations can be determined based on the combinations of fluorescent intensities of the beads from the two (or more) dyes after excitation by light (e.g., laser light). The bead populations can form a virtual multidimensional array based on the quantities of the two (or more) fluorescent dyes present on or in the beads (and corresponding fluorescent intensities from the fluorescent dyes). Such an array can be used in a variety of assays, including multiplex, multi-analyte assays for the simultaneous detection of two or more analytes by, for example, flow cytometry.

Fluorescently labeled reporter reagents, one for each species of analytes to be detected and quantified, can be used to quantify analytes. The reporter reagents can be labeled with the same fluorescent dye. For example, the bead populations and fluorescently labeled reporter reagents, one for each species of analytes to be detected and quantified, can be incubated with a sample containing (or suspected of containing) the analytes of interest to allow for the formation of bead-analyte-reporter complexes for each analyte species present. The resulting complexes can be analyzed by flow cytometry to identify (e.g., based on the fluorescence intensities of the two fluorescent dyes present on the beads) and quantify (e.g., based on the fluorescence intensity of the fluorescent dye present on all the reporter reagents) the analytes present in the sample.

The beads of each bead population can be coated with a capture reagent, such as a unique analyte-specific binding agent (e.g., a monoclonal antibody (mAb)). The identities of the analytes detected can be determined based on the identities of the beads populations, which in turn can be determined based on the quantities of fluorescence of the beads in the bead populations from the one fluorescent dye or the two (or more) fluorescent dyes. Reporter reagents, one for each analyte or analyte species (such as a second analyte-specific binding agent, including a mAb), labeled with the same fluorescence dye can be used to quantity the analytes present in a sample because the identity of the analyte can be determined based on the identity of the bead the analyte is bound to. Because the identity of the analyte bound to the complex is indicated by the identity of the bead, multiple analytes can be simultaneously detected using the same fluorophore for all reporter reagents.

Arrays, such as virtual multidimensional arrays, can be used for measurement of a variety of soluble and intracellular proteins, such as, for example, cytokines, chemokines, growth factors, and phosphorylated cell signaling proteins. For example, multiplexed analysis of 30 proteins can be performed with a two-dimensional bead populations with different quantities of two fluorescent dyes and reporter reagents with the same fluorescent dye. Three fluorescent dyes can be used to detect and quantity 30 proteins in a sample in this example. In some embodiments, the multiplexing enabled by the arrays (e.g., cytometric bead arrays) advantageously requires only a small amount of sample is required (e.g., 25 to 50 µL of sample), while maximizing the number of proteins that can be analyzed. In some embodiments, the beads (e.g., capture beads) contain unique amounts of a single red dye. The unique spectral properties of this dye can enable analysis of samples on flow cytometers that have a single 488-nm laser or on dual-laser (488-nm or 532-nm and 633-nm) flow cytometers. In some embodiments, the beads (e.g., capture beads) contain unique amounts of two dyes.

Figure 4:
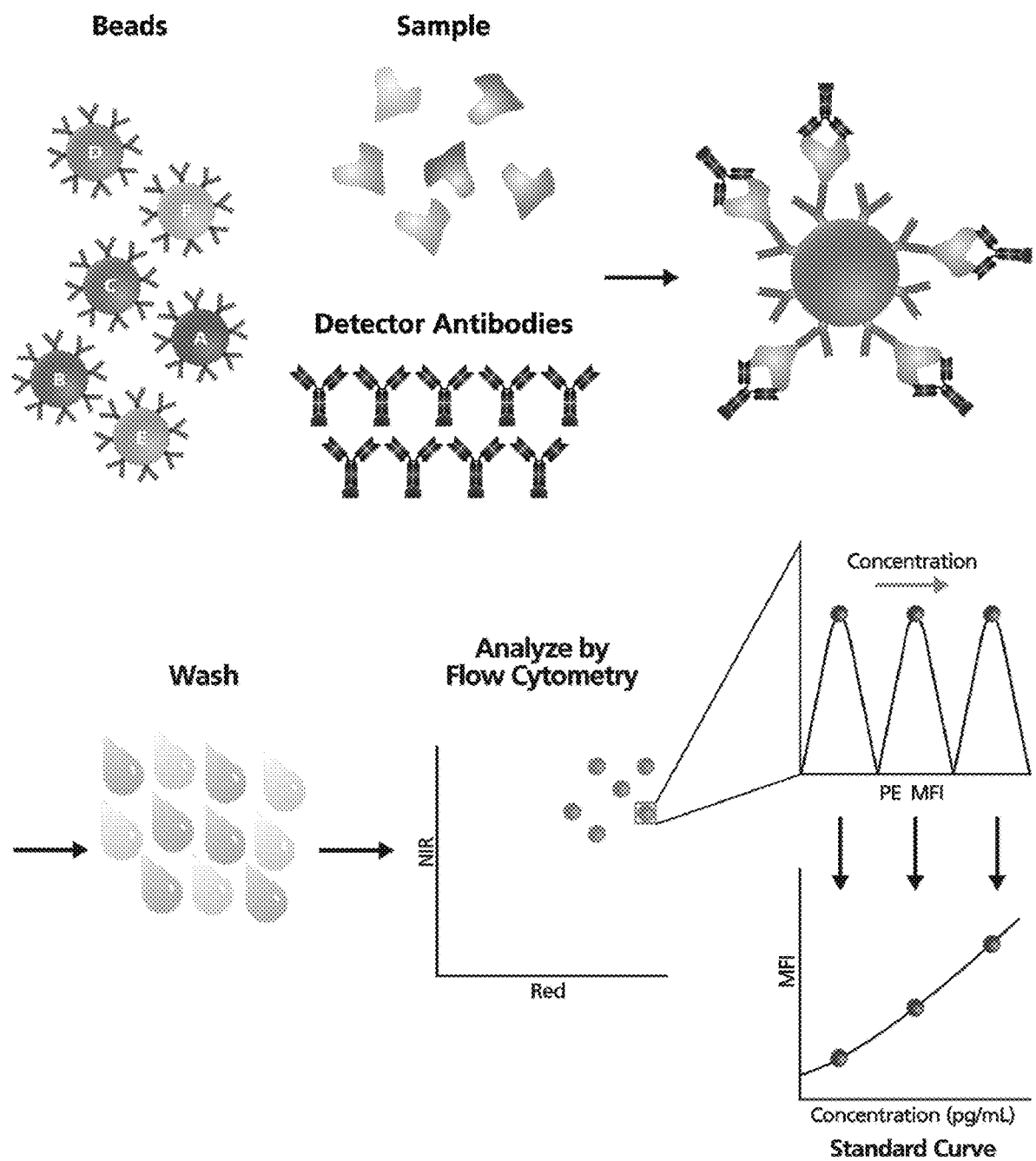
FIG. 4 shows a non-limiting exemplary workflow of using a bead array, such as a cytometric bead array (CBA), to measure analytes in a sample.

FIG. 4 shows a non-limiting exemplary workflow of using a bead array, such as a cytometric bead array (CBA), to measure analytes (e.g., soluble and intracellular proteins) in a sample. Capture beads of one capture bead population can be coated with a capture antibody (or capture antibody molecules) specific for a single analyte. Capture beads of different capture bead populations can be coated with capture antibodies specific for different analytes. Capture beads in one capture bead population can have a unique fluorescence intensity profile (e.g., from a single fluorescent dye or a combination of two (or more) fluorescent dyes). Capture beads in different capture bead populations can have different fluorescence intensity profiles (illustrated by different letters). In some embodiments, the capture beads can contain unique amounts of a single fluorescent dye (e.g., a red dye). In some embodiments, the capture beads can contain unique amounts of two (or more) fluorescent dye (e.g., a red dye and an NIR dye). A combination of different beads can be mixed with a sample and a mixture of detection antibodies that are conjugated to a reporter molecule (e.g., phycoerythrin (PE)). A combination of different beads can be mixed with controls or standards of known concentration and the mixture of detection antibodies that are conjugated to the reporter molecule (e.g., phycoerythrin (PE)). Following incubation and subsequent washing, the samples can be analyzed on a flow cytometer.

An array can contain a plurality of bead populations, wherein different populations are labeled, using the same fluorophore, at a plurality of discrete fluorescence levels. The fluorescence properties of the virtual multidimensional arrays can enable the identification of the beads in each population by exposing the array to excitation light and measuring the fluorescence of each bead in one detection channel for the fluorophore. The resulting fluorescence intensity data with respect to the fluorophore (and channel) can be plotted in a dimensional dot-plot, with intensity of the detection channel on one axes. Each population can appear as cluster uniquely positioned in the dot plot. The fluorophore used for identifying the beads (and thus the analytes bound to the beads) is referred to herein as a clustering fluorescent dye. The fluorescent intensities of the fluorophore detected are referred to herein as clustering fluorescence intensities.

Washing. The microparticles can be washed, e.g., to remove any unbound detector molecules and other sample components. Washing can be performed using any convenient protocol, e.g., by combining the reaction mixture with a suitable wash buffer and separating the microparticles from the fluid. A given washing protocol can include one or more distinct washing steps, as desired. Following any washing protocol, the microparticles can be re-suspended in a suitable liquid, e.g., the washing buffer or another buffer, for flow cytometric analysis.

Flow Cytometry. An array, such as the virtual multidimensional array illustrated in FIG. 4, can contain a plurality of bead populations, wherein different populations are labeled, using the same two fluorophores, at a plurality of discrete fluorescence levels for each of the two fluorophores. The fluorescence properties of the arrays can enable the identification of the beads in each population by exposing the array to excitation light and measuring the fluorescence of each bead in each of two detection channels, one for each of the two fluorophores. The beads in the array can be detected and uniquely identified by exposing the beads to excitation light and measuring the fluorescence of each bead in each of the two detection channels. The excitation light can be from one or more light sources and can be either narrow or broadband. Examples of excitation light sources include lasers, and light emitting diodes. For identification of beads in the arrays, two detector channels can be used. The detector channels can be non-overlapping channels or partially overlapping. A flow cytometer can have two channels used to detect bead fluorescence and a third channel is used to detect reporter fluorescence.

The beads from the reaction mixture can be flow cytometrically assayed to detect the presence and/or to determine the quantity of an analyte in the sample. Flow cytometry uses multi-parameter data for identifying and distinguishing between different particle types (i.e., particles that vary from one another terms of label (wavelength, intensity), size, etc., in a fluid medium. A liquid medium comprising the beads can first introduced into the flow path of the flow cytometer. When in the flow path, the beads can pass substantially one at a time through one or more sensing regions, where each of the beads is exposed individually to a source of light at a single wavelength (or a single source of light at multiple wavelengths, or multiple sources of light at multiple wavelengths) and measurements of light scatter parameters and/or fluorescent emissions as desired (e.g., two or more light scatter parameters and measurements of one or more fluorescent emissions) are separately recorded for each bead. The data recorded for each bead can be analyzed in real time or stored in a data storage and analysis means, such as a computer, as desired.

Detectors (e.g., light collectors, such as photomultiplier tubes (or "PMT")) in a sensing region can record light that passes through each bead (generally referred to as forward light scatter), light that is reflected orthogonal to the direction of the flow of the beads through the sensing region (referred to as orthogonal or side light scatter) and fluorescent light emitted from the beads, if the bead is labeled with fluorescent marker(s), as the bead passes through the sensing region and is illuminated by the energy source. Each of forward light scatter (or FSC), orthogonal light scatter (SSC), and fluorescence emissions (FL1, FL2, etc.) can comprise a separate parameter for each bead (or each "event"). Thus, for example, two, three or four parameters can be collected (and recorded) by two, three or four detectors from a bead labeled with two different fluorescence markers. In some embodiments, beads from two bead populations can have different sizes, such that the beads can be distinguished by their FSC and SSC characteristics.

A microparticle array (e.g. a cytometric bead array) can include populations of microparticles (e.g., beads), wherein each microparticle is labeled with a single fluorescent dye. The array can comprise a plurality of microparticle populations. In some embodiments, microparticle populations are labeled, using the same fluorophore, such that each population exhibits a measurably distinct mean fluorescence intensity. In some embodiments, microparticle populations in different sets of microparticle populations are labeled with different fluorescent dyes, wherein all of the fluorescent dyes can be excited by the same excitation light, the emission spectra of each dye is detectable using the same two detection channels, and the relative amount of emissions in each of the two detection channels is distinguishably distinct between different dyes.

Fluorescence emitted in detection channels used to identify the microparticles can be measured following excitation with a single light source, or can be measured separately following excitation with distinct light sources. If separate excitation light sources are used to excite the microparticle dyes, the dyes preferably are selected such that all the dyes used to construct the array are excitable by each of the excitation light sources used. For example, a dual laser flow cytometer can have 488 nm and 635 nm excitation lasers that are focused on the flow stream at spatially discrete regions, and detection optics designed to measure light in three detection channels, designated FL1, FL2, and FL3, following excitation by the 488 nm laser, and a fourth detection channel, designated FL4, following excitation by the 635 nm laser. In some embodiments, FL3 and FL4 are selected as the two detection channels used to identify the microparticle populations. For example, one channel, FL3, can be measured following excitation by the 488 nm laser and the second channel, FL4, can be measured following excitation by the 635 nm laser. The selection of dyes and detection channels in can be made in view of the configuration of an existing commercial instrument. Alternatively, a flow cytometer could be configured to measure emission in both FL3 and FL4 following excitation with a single laser.

Analysis. The resulting fluorescence intensity data with respect to the two fluorophores (and channels) can be plotted in a two-dimensional dot-plot, with intensity of the two detection channels on the two axes (See FIG. 4 for an illustration). Each population can appear as cluster uniquely positioned in the two-dimensional dot plot. The two fluorophores used for identifying the beads (and thus the analytes bound to the beads) are referred to herein as clustering fluorescent dyes. The fluorescent intensities of the two fluorophores detected by, for example, the two detection channels, are referred to herein as clustering fluorescence intensities. The identity of the microparticle populations, determined from the microparticle fluorescence measured in the two detection channels, enables identification of the analyte bound to the microparticle through the analyte-specific reagent.

A plurality of gates for each bead population can be determined based on the fluorescence intensities detected by the two detection channels for the two fluorophores. Methods for determining a plurality of gates for cytometric event data have been described in U.S. Pat. No. 8,990,047, U.S. Patent Application publication No. 2014/0343897, U.S. Patent Application publication No. 2017/0061657, U.S. Provisional Application No. 62/663,086, U.S. Provisional Application No. 62/724,834, U.S. Provisional Application No. 62/739796, U.S. Provisional Application No. 62/747,004, and U.S. Provisional Application No. 62/817,555; the content of each of these applications is incorporated herein by reference in its entirety. The correspondence of event data to the bead populations (and thus the analytes detected) can be determined based on the quantities (and thus the fluorescence intensities detected and/or expected) of two (or more) fluorescent dyes associated with the beads of a bead population.

The quantity of each analyte can be determined based on the fluorescence intensities from molecules of a reporter reagent for the analyte. For example, the median fluorescence intensity (MFI) of the fluorescence intensities from molecules of the reporter reagent for the analyte can be used to determine the concentration of the analyte in the sample using a standard curve. A standard curve of the correspondence between the median fluorescence intensity (MFI) and the concentration of the analyte can be determined as disclosed herein using samples of known concentrations of the analyte. The quantities of analytes in a sample can be determined based on the fluorescence intensities of the single fluorescent dye conjugated to the reporter reagents.

For example, the median fluorescence intensities (MFIs) of the fluorescence intensities from molecules of the reporter reagents for the analytes can be used to determine the concentration of the analyte in the sample using standard curves. Standard curves of the correspondence between the MFIs and concentration of analytes can be determined using samples of known concentrations of the analytes.

Fluorophores. Fluorescent dyes (fluorophores) suitable for use in disclosed methods and methods can be selected from any of the many dyes suitable for use in imaging applications (e.g., flow cytometry). Dyes employed to label microparticle populations in the different sets of bead populations can be selected such that the emission spectra of each dye is detectable using the same two detection channels, and the relative amount of emissions in each of the two detection channels is distinguishably distinct between different dyes. The spillover of the microparticle emissions into the channel used to measure the reporter fluorescence with the one or two channels used to measure the fluorescent intensities used to identify the beads can be minimized. The two channels used for detecting the microparticle emission can spectrally separated from the reporter channel, and the dyes used have minimal spillover of the microparticle emissions into the reporter channel.

The microparticles or beads can include one or more fluorescent dyes incorporated therein, i.e., the microparticles or beads are stained with one or more fluorescent dyes. Fluorescent dyes have been incorporated into uniform microspheres in a variety of ways, for example by copolymerization of the fluorescent dye into the microspheres during manufacture; by entrapment of the fluorescent dye into the microspheres during the polymerization process; or by non-covalent incorporation of the fluorescent dye into previously prepared microspheres.

Samples. A variety of different types of samples can be assayed with the compositions and methods provided herein. Samples that can be assayed can vary, and include both simple and complex samples. Simple samples can comprise samples that include an analyte of interest, and may or may not include one or more molecular entities that are not of interest, where the number of these non-interest molecular entities can be low, e.g., 10 or less, 5 or less, etc. Simple samples can include initial biological or other samples that have been processed in some manner, e.g., to remove potentially interfering molecular entities from the sample, inhibit proteases, etc. Complex samples may or may not have the analytes of interest, but can comprise many different proteins and other molecules that are not of interest. In some embodiments, a complex sample comprises 10 or more, such as 20 or more, including 100 or more distinct (i.e., different) molecular entities, that differ from each other in terms of molecular structure. The sample can be any of a variety of different types of samples, where the sample can be used directly from an initial source as is, e.g., where it is present in its initial source as a fluid, or preprocessed in some manner, e.g., to provide a fluid sample from an initial non-fluid source, e.g., solid or gas; to dilute and or concentrate an initial fluid sample, etc. Samples of interest include, but are not limited to: biological fluids, e.g., blood, tears, saliva; biological solids that are treated to produce fluid samples, e.g., tissues, organs, etc., which are subjected to one or more processing steps, e.g., homogenization, etc., to produce a fluid sample; etc. In some embodiments, the samples of interest are biological samples, such as, but not limited to, urine, blood, serum, plasma, saliva, perspiration, feces, cheek swabs, cerebrospinal fluid, cell lysate samples, and the like. The sample can be a biological sample or can be extracted from a biological sample derived from humans, animals, plants, fungi, yeast, bacteria, tissue cultures, viral cultures, or combinations thereof using conventional methods for the successful extraction of DNA, RNA, proteins and peptides. In some instances, the sample is a cell lysate prepared from an initial cellular sample. In some such embodiments, any suitable lysing protocol can be employed, e.g., contacting a cellular sample with a lysing agent and separating the resultant cellular debris from the supernatant to obtain a cell lysate. Many cell lysates can comprise proteases that must be inhibited to accurately detect an analyte of interest.

As used herein, the terms "microparticles", "microbeads", or "beads" can refer to small particles with a diameter in the nanometer to micrometer range, typically about 0.01 to 1,000 $\mu$m in diameter. Microparticles can be of any shape. In some embodiments, microparticles are approximately spherical ("microspheres"). Microparticles can serve as solid supports or substrates to which other materials, such as target-specific reagents, reactants, and labels, can be coupled. Microparticles can be made of any appropriate material (or combinations thereof), including, but not limited to polymers such as polystyrene; polystyrene which contains other co-polymers such as divinylbenzene; polymethylmethacrylate (PMMA); polyvinyltoluene (PVT); copolymers such as styrene/butadiene, styrene/vinyltoluene; latex; or other materials, such as silica (e.g., $SiO_2$).

As used herein, the term "microparticle population" can refer to a group of microparticles that possess essentially the same optical properties with respect to the parameters to be measured, such as synthesized microparticles that, within practical manufacturing tolerances, are of the same size, shape, composition, and are labeled with the same kind and amount of dye molecules. For example, unlabeled microparticles, microparticles labeled with a first dye at a first concentration, microparticles labeled with the first dye at a second concentration, and microparticles beads labeled with a second dye at the third concentration could constitute four distinct bead populations.

The microparticles can be detected using instruments that have the ability to detect fluorescence light emitted in defined frequency ranges, referred to as "detector channels" or "detection channels." Such instruments contain multiple photodetectors, such as photomultiplier tubes or photodiodes, and the range of wavelengths detected by each photodetector is determined by the use of frequency-dependent filters, dichroic mirrors, or other dispersive elements, as is well known in the art. Alternatively, the same detector can be used for multiple frequency ranges by changing the dispersive elements during analysis, as is typical in fluorescence microscopy.

As used herein, the term "analyte" can refer to any substance to be analyzed, detected, measured, or labeled. Examples of analytes include, but are not limited to: proteins, peptides, hormones, haptens, antigens, antibodies, receptors, enzymes, nucleic acids, polysaccharides, chemicals, polymers, pathogens, toxins, organic drugs, inorganic drugs, cells, tissues, microorganisms, viruses, bacteria, fungi, algae, parasites, allergens, pollutants and combinations thereof. It will be understood that detection of, for example, a cell, is typically carried out by detecting a particular component, such as a cell-surface molecule, and that both the component and the bacteria as a whole can be described as the analyte.

As used herein, the terms "analyte-specific reagent" or "target-specific reagent" can refer to any reagent that preferentially binds to an analyte or target of interest, relative to other analytes potentially present in a sample. A target (analyte) and target-specific (analyte-specific) reagent can be members of a binding pair, and either member of the pair can be used as the target-specific reagent in order to selectively bind to the other member of the pair. Examples of target and target-specific reagent pairs include, but are not limited to, antigen and antigen-specific antibody; hormone and hormone receptor; hapten and anti-hapten; biotin and avidin or steptavidin; enzyme and enzyme cofactor; and lectin and specific carbohydrate.

Bead Array Analysis Workflow

A cytometer can measure a variety of soluble and intracellular proteins, including cytokines, chemokines, growth factors, and phosphorylated cell signaling proteins using flow cytometry. A bead-based immunoassay assay, such as the BD™ (Franklin Lakes, N.J.) Cytometric Bead Array, can enable analysis of, for example, 30 proteins using just 25 to 50 μL of sample in comparison to other methods such as enzyme-linked immunosorbent assay (ELISA) and Western blot, which enable only one protein to be analyzed per sample at a time.

Disclosed herein include embodiments of a method or a workflow for cytometric bead array (CBA) analysis. The method can be implemented as a software plugin, such as a plugin of a flow cytometry data analysis program, bioinformatics platform, or bioinformatics solution, such as FlowJo® (Ashford, OR). The plugin can have direct integration into the flow cytometry data analysis program. The CBA plugin can analyze data from any CBA standard assay. The plugin can implement an intuitive method or workflow for the analysis of cytometric bead array data. The plugin can integrate directly into a bioinformatics platform (e.g., FlowJo® (Ashford, Oreg.)) and produce analysis output within that bioinformatics platform. The plugin can be an add-in plugin for a bioinformatics solution (e.g., FlowJo® (Ashford, Oreg.)). The plugin can be published or available on a plugin exchange (e.g., FlowJo Exchange). The functionalities of the plugin can include data analysis, auto-gating, peak-finding, calibration to standards, etc. The plugin can include an application programming interface (API) for implementing additional functionalities. The plugin can be implemented using API of the flow cytometry data analysis program. The plugin can be integrated into the interface of the flow cytometry data analysis program. In some embodiments, the plugin can include peak finder, peak gating, and regression functionalities. The plugin can have universal compatibility with all bead-based assays, including all CBA kits.

Figure 5:
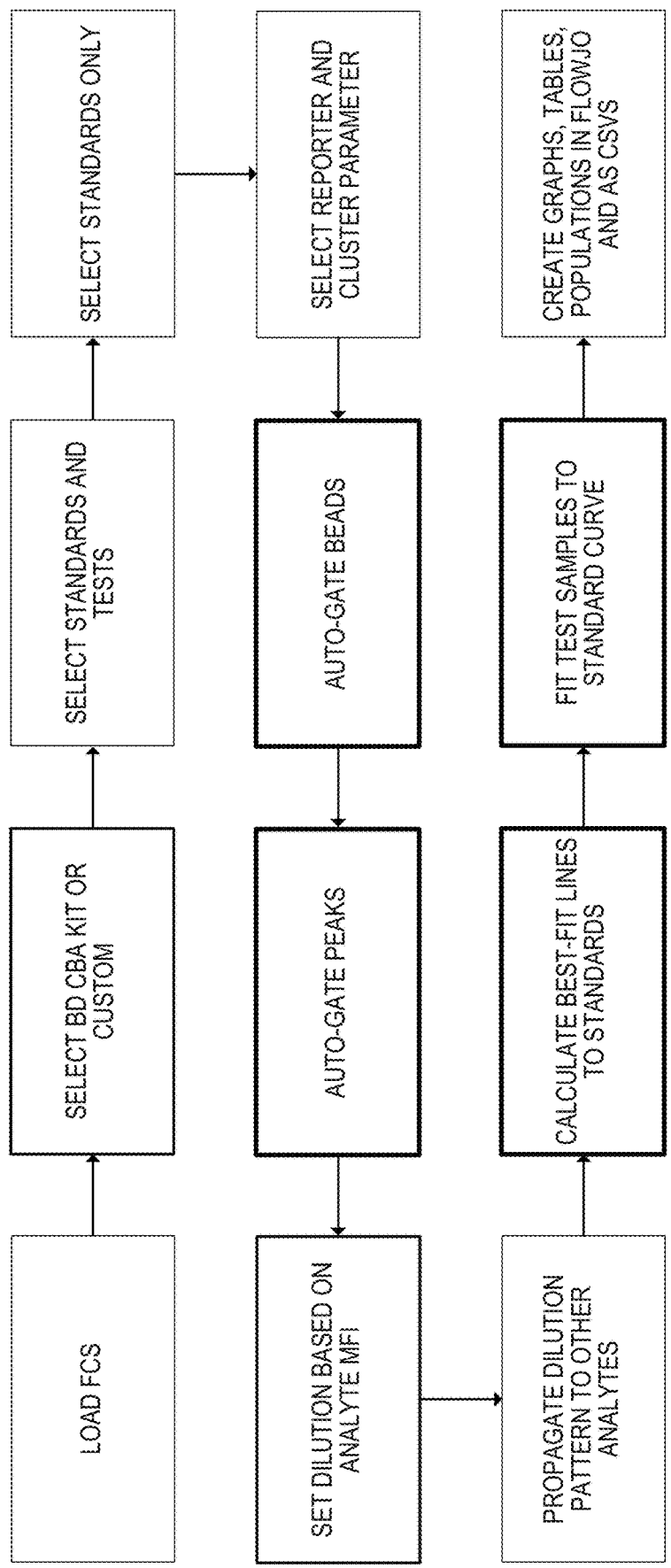
FIG. 5 is a diagram showing an exemplary workflow of bead array analysis (e.g., cytometric bead array analysis).
Figure 6A:
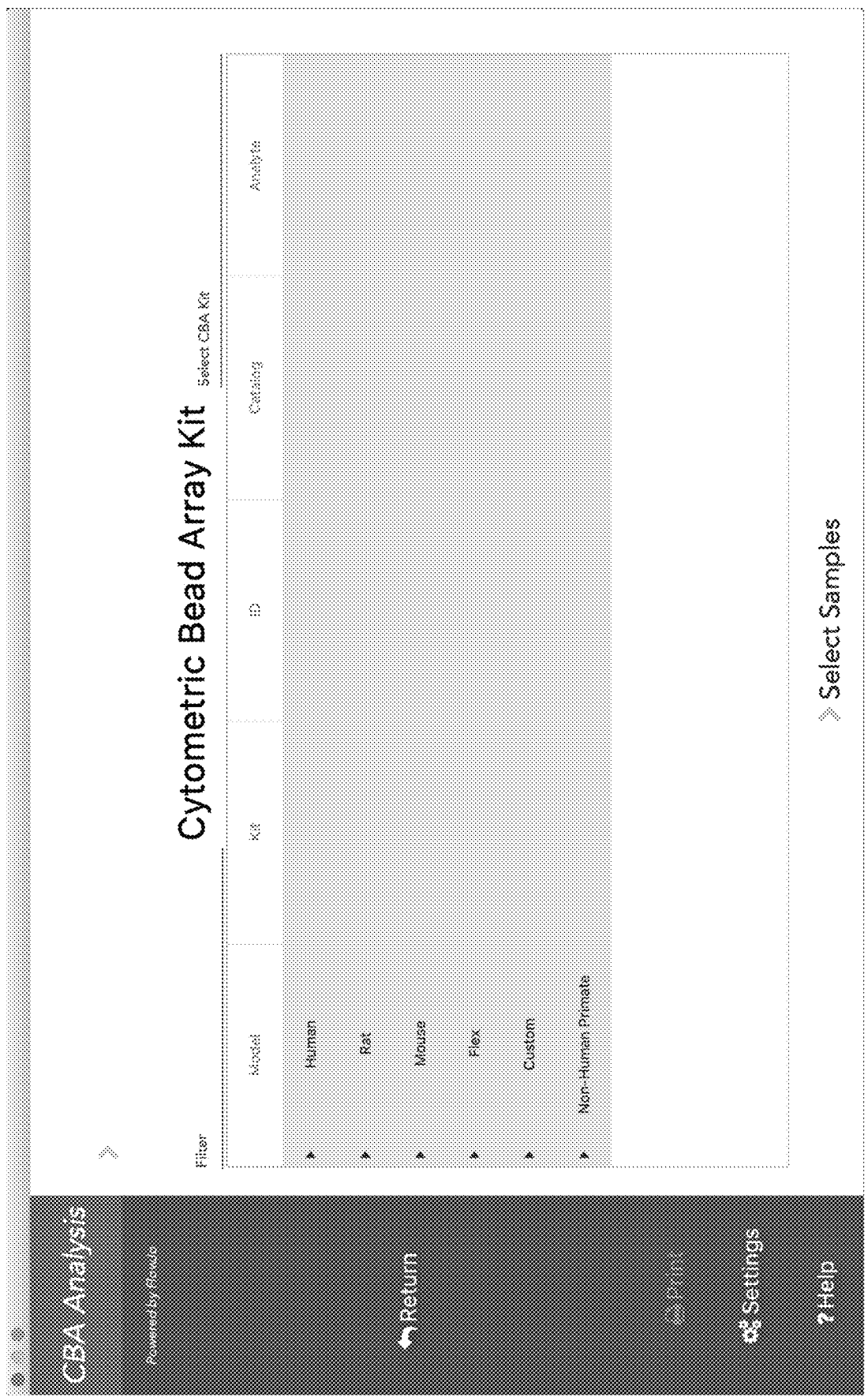
Figure 6C:
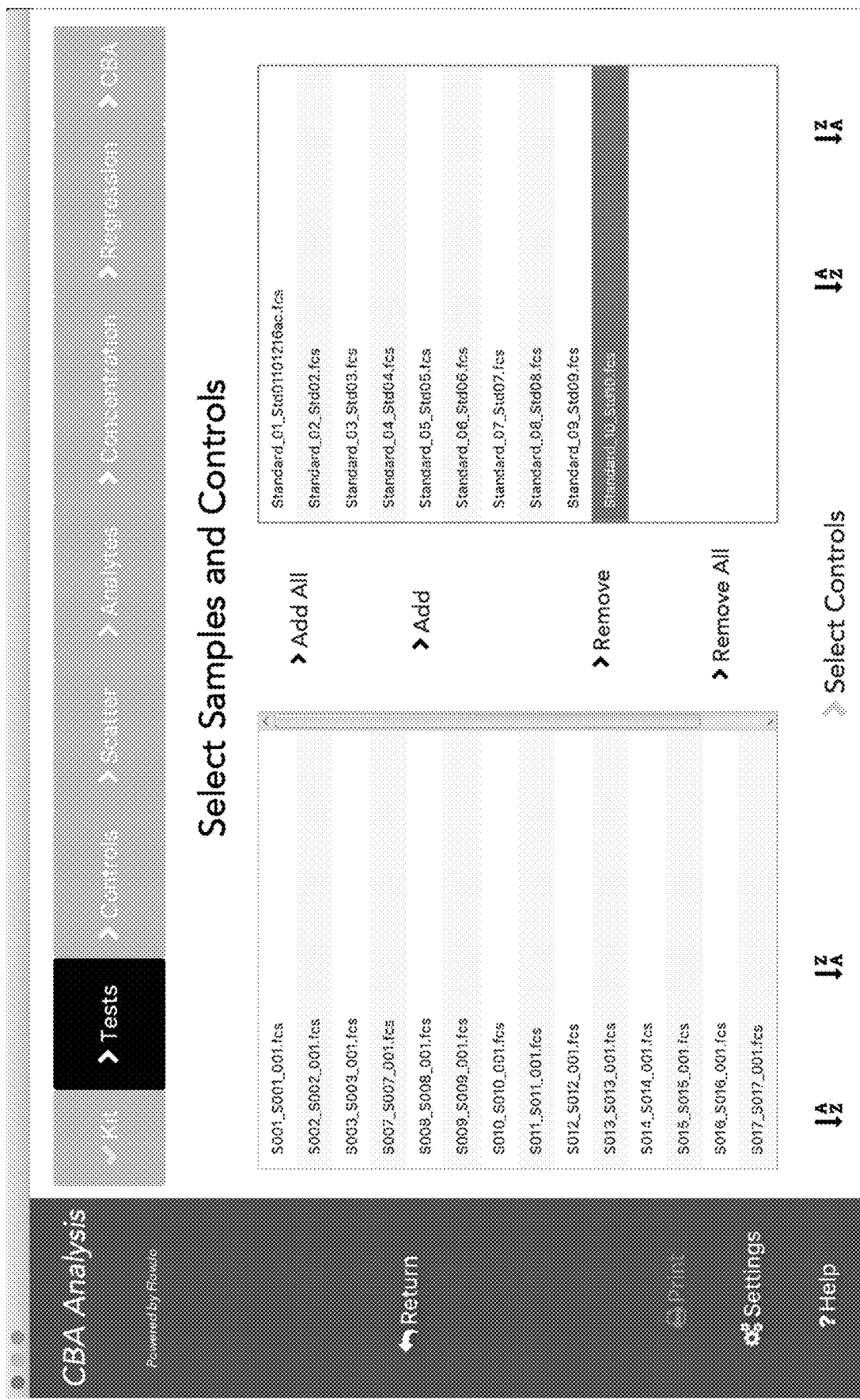
Figure 6D:
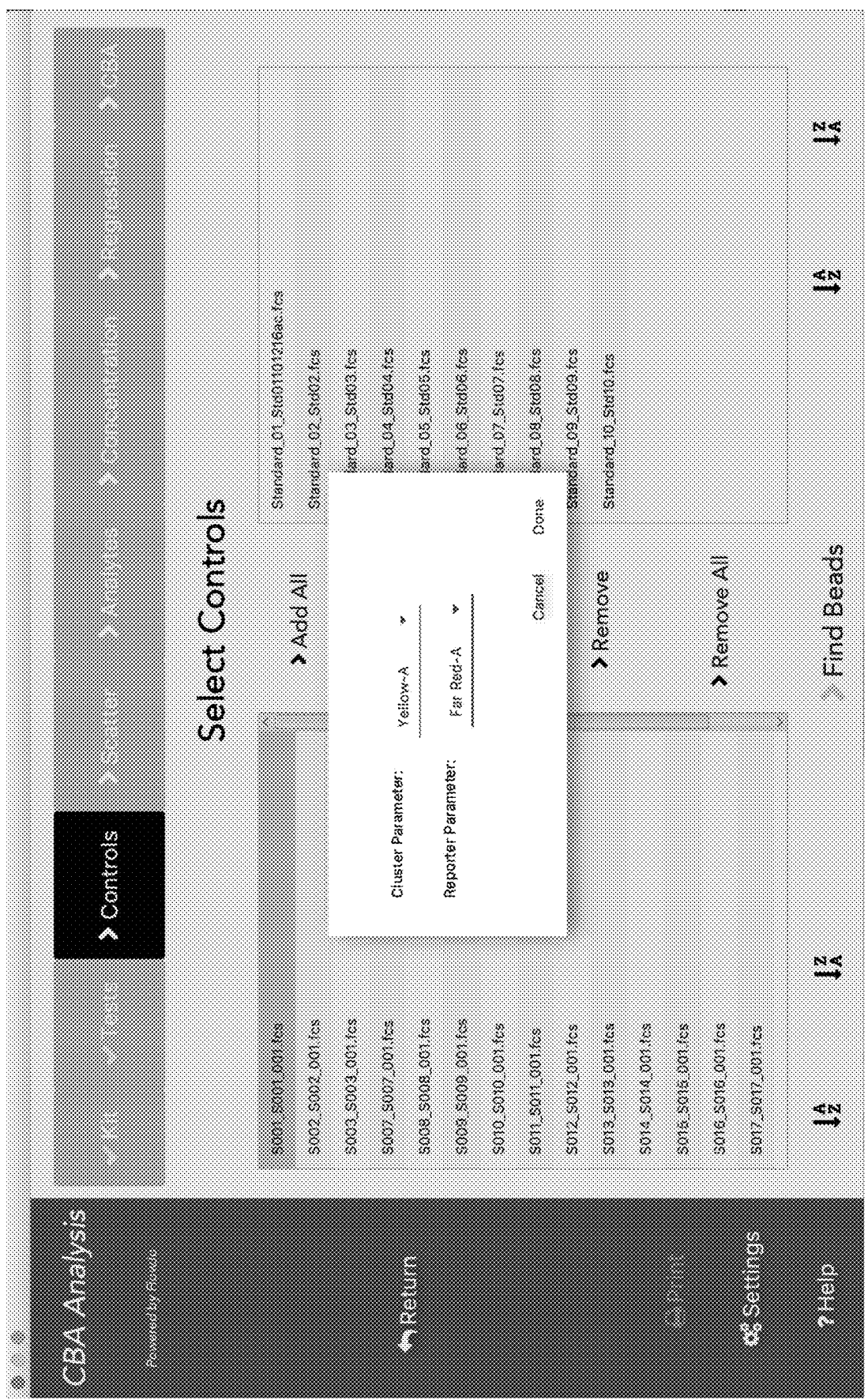
Figure 6E:
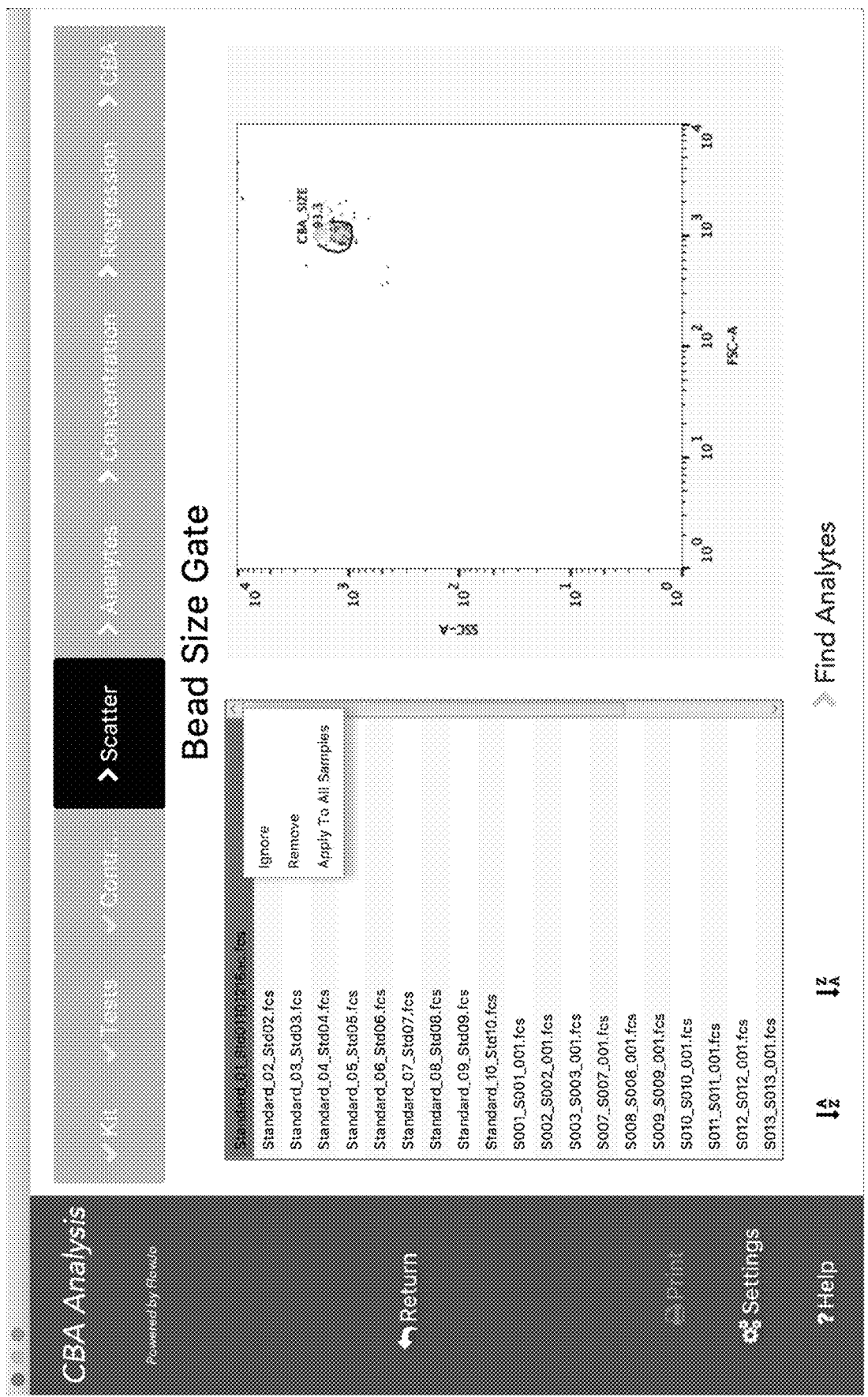
Figure 6F:
Figure 6H:
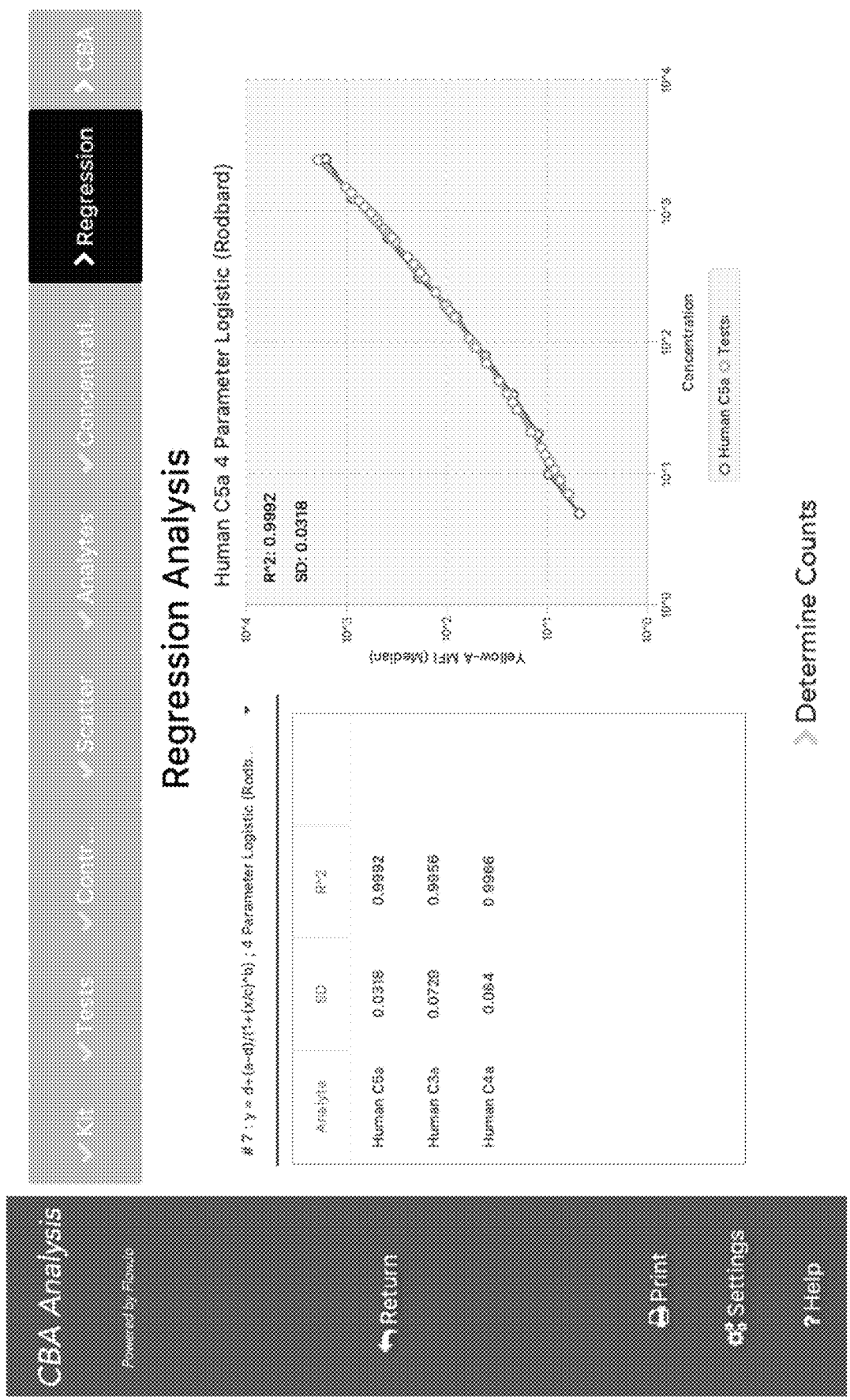
Figure 7A:
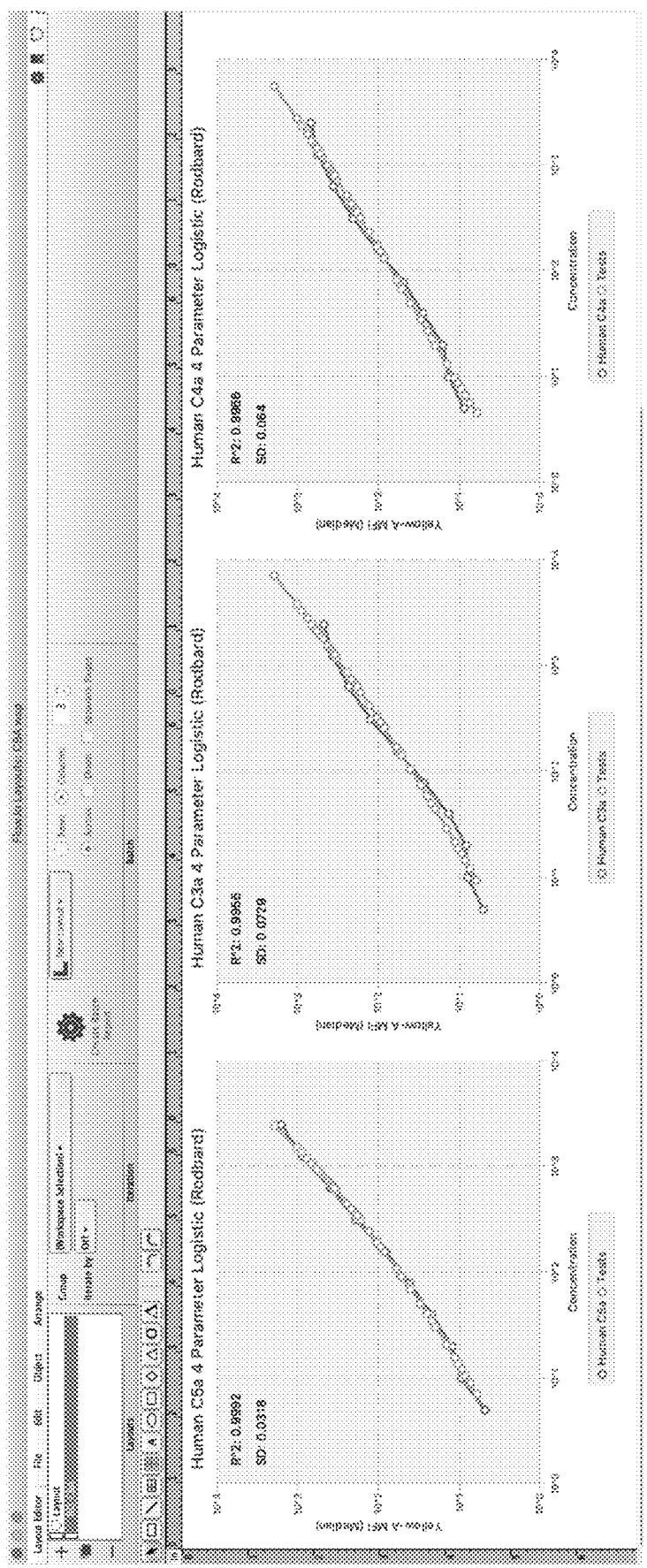
Figure 7B:
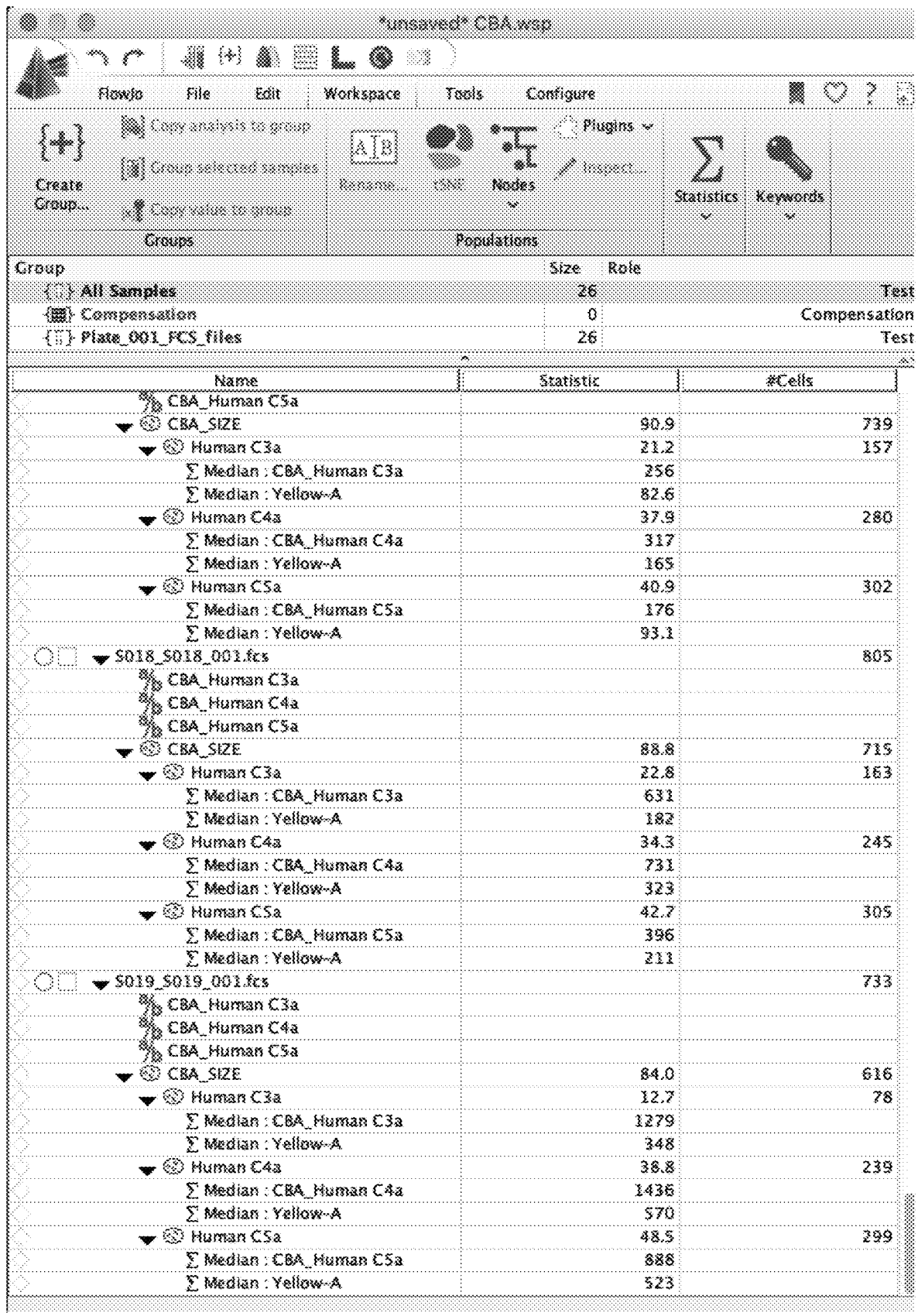
Figure 7E:
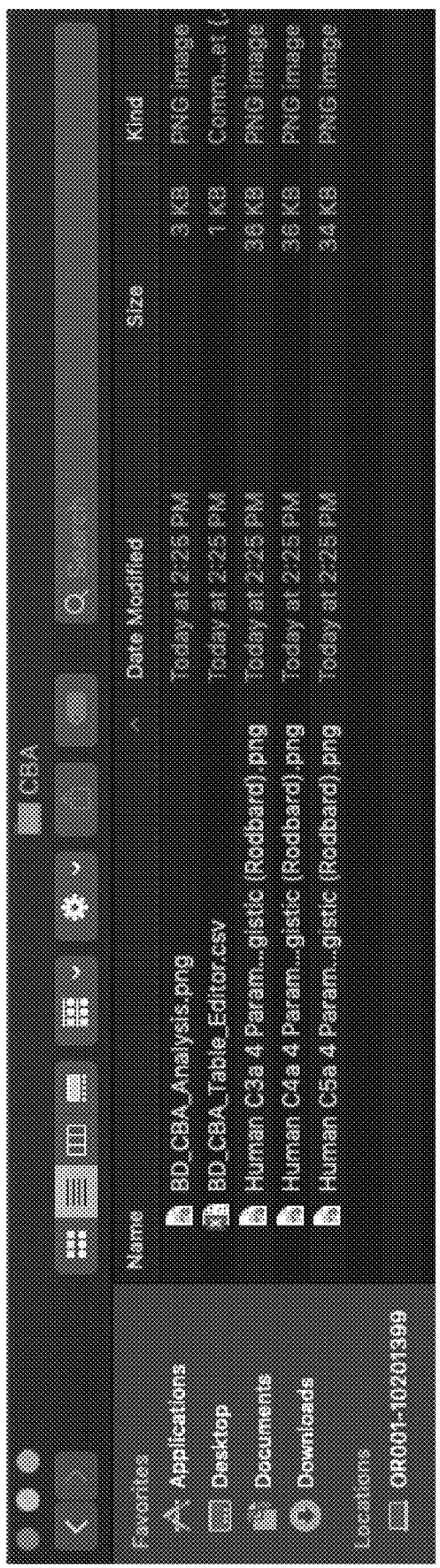

FIG. 5 is a diagram showing an exemplary method or workflow of cytometric bead array analysis, for example, implemented by a plugin. The CBA analysis workflow can be a multi-step workflow. In some embodiments, the method can include some or all of the following steps.

Select a kit

Choose samples to analyze Segregate controls form test samples

Confirm clustering and reporter parameters

Adjust auto-gating and peak finding (beads and peaks respectively) Input standards per analyte Use median population statistics to generate standard curve based on user selected fitting function Output results ("analyses") automatically into analysis "Workspace, such as calibrated parameters for analyte concentration, tables, and figures In some embodiments, the method can be used to analyze CBA data from CBA kits form BD™ (Franklin Lakes, N.J.) Cytometric Bead Array and data from other bead-based immunoassays (e.g., LEGENDplex™ from BioLegend (San Diego, Calif.)). The method can work with any bead-based immunoassay through a "Custom" option that is not limited to a particular manufacturer.

In some embodiments, the method can include setting dilution based on median fluorescence intensity (MFI). The method can allow for parsing of dilution from flow cytometry standard (FCS) keywords. The method can allow a user to set dilution series.

In some embodiments, the method can include autogating peaks (e.g., peaks corresponding to fluorescent intensities from the fluorescent dye of the reporter reagents). For example, the method can include finding peaks in univariate histogram. The method can include modeling flow cytometry data closely, for example, by finding peaks on log or biexponential axis.

In some embodiments, the method can include autogating beads (e.g., fluorescent intensities from the fluorescent dye(s) of the beads used in the bead-based immunoassay. For example, the method can include using peak anatomy to set gates. The method can tweak gates minimum and maximum to set a uniform interval on a log or biexponential axis. The method can include setting color based on the interval (e.g., a uniform interval).

In some embodiments, the method can include calculating best-fit lines. For example, the method can implement six different best-fit lines, such as linear, $2^{nd}$ and $3^{rd}$ degree polynomial, Power, 4-Parameter logistic and Gamma Variate. In some embodiments, the method can include fitting test samples to standard curves. For example, the method can include using best-fit curve to calculate concentration from MFI. The method can include converting MFI using a formula of a standard to a derived parameter. The method can include creating statistics for each analyte.

In some embodiments, the method can facilitate data analysis of bead assays. These assays can detect the presence of, or determine concentrations for, multiple analytes (for example, proteins and peptides) in a sample. In some embodiments, the method can implement a user interface to facilitate data analysis.

FIG. 6A-6I are non-limiting exemplary illustrations of a user interface design for a cytometric bead array analysis workflow. In some embodiments, the workflow can be intuitive for analyzing data. The user interface design can include a step-through "wizard" workflow. For example, a user can only proceed to the next step if all necessary options have been filled or satisfied. Modal dialogs can inform user of quality of selections. Quality of selections can be measured dynamically to avoid downstream issues. FIG. 10A-10F are additional, non-limiting exemplary illustrations of a user interface design for a cytometric bead array analysis workflow.

FIG. 7A-7E are non-limiting exemplary illustrations of a user interface design for outputting the result of cytometric bead array analysis. In some embodiments, the plugin can automatically create outputs in the flow cytometry data analysis program. For example, the plugin can generate best fit graphs in the layouts of the flow cytometry data analysis program. Populations, statistics and derived parameters can be generated in the workspace of the flow cytometry data analysis program. In some embodiments, the plugin can generate statistics a CSV format and in a Table Editor of the flow cytometry data analysis program. FIG. 11A-11E are additional non-limiting exemplary illustrations of a user interface design for outputting the result of cytometric bead array analysis.

Bead Array Analysis

Figure 8:
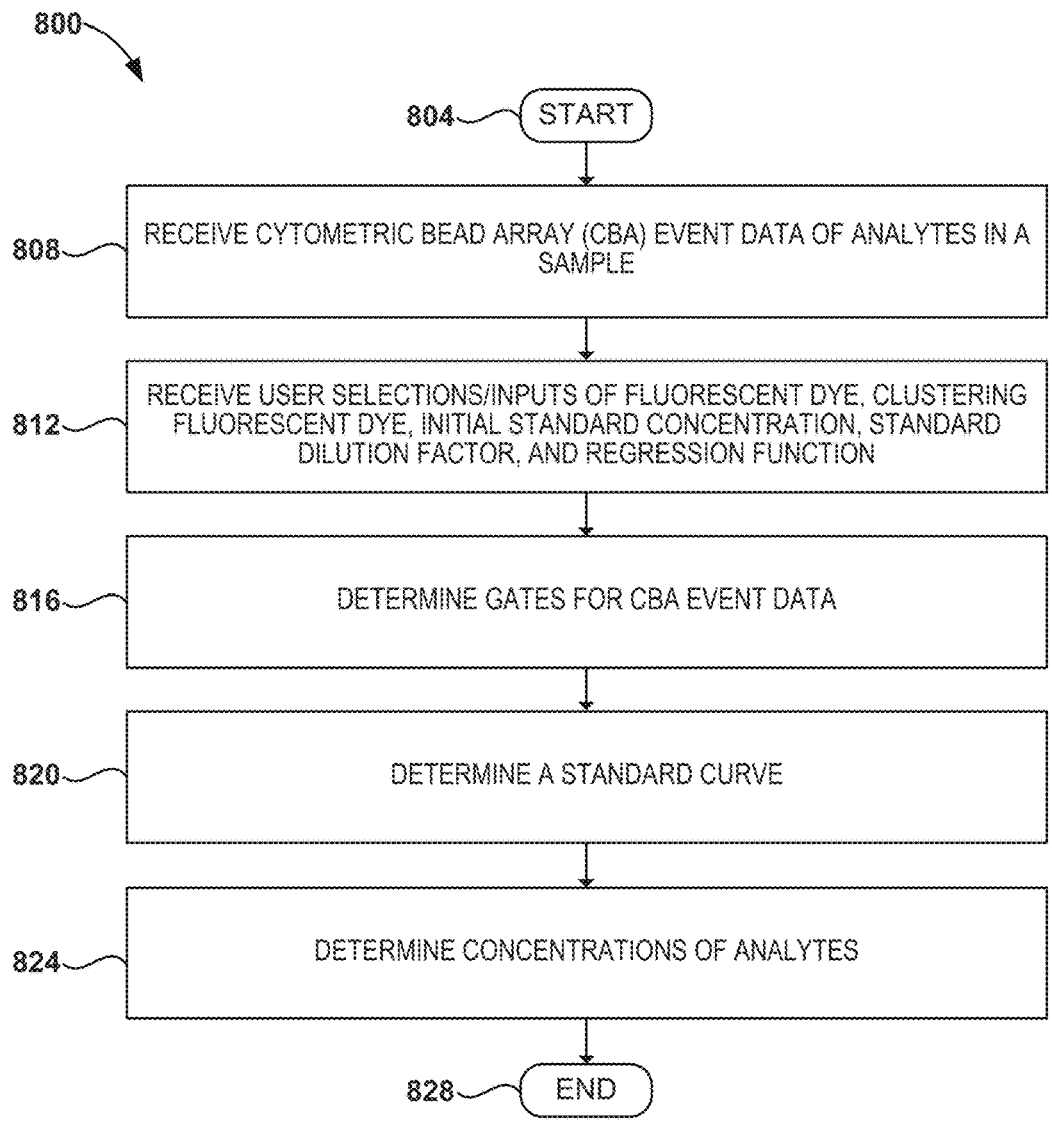
FIG. 8 is a flow diagram showing an exemplary method of performing bead array analysis.

FIG. 8 is a flow diagram showing an exemplary method 800 of performing bead array analysis (such as cytometric bead array analysis). The method 800 may be embodied in a set of executable program instructions stored on a computer-readable medium, such as one or more disk drives, of a computing system. For example, the computing system 900 shown in FIG. 9 and described in greater detail below can execute a set of executable program instructions to implement the method 800. When the method 800 is initiated, the executable program instructions can be loaded into memory, such as RAM, and executed by one or more processors of the computing system 900. Although the method 800 is described with respect to the computing system 900 shown in FIG. 9, the description is illustrative only and is not intended to be limiting. In some embodiments, the method 800 or portions thereof may be performed serially or in parallel by multiple computing systems.

After the method 800 begins at block 804, the method 800 proceeds to block 808, where a computing system can receive or retrieve cytometric bead array (CBA) event data of a plurality of events corresponding to a plurality of samples and a plurality of standards (or controls), wherein each of the plurality of events is associated with (1) a reporter fluorescent intensity of a reporter fluorescent dye associated with a reporter antibody, (2) a clustering fluorescent intensity of a clustering fluorescent dye associated with a bead in the CBA event data.

In some embodiments, each of the plurality of events is associated with a combination of clustering fluorescent intensities of at least two clustering fluorescent dyes associated with the bead in the CBA event data, and wherein two different combinations of clustering fluorescent intensities of the at least two clustering fluorescent dyes associated with the two events of the plurality of events identify the two analytes of the plurality of analytes.

In some embodiments, a sample of the plurality of samples comprises the plurality of analytes each at a sample concentration. A standard of the plurality of standards can comprise each of the plurality of analytes each at a standard concentration. Two standards of the plurality of standards can comprise two different standard concentrations of each of the plurality of analytes.

In some embodiments, the bead is associated with a clustering antibody capable of binding to an analyte of the plurality of analytes. Two beads of the beads can comprise different (1) quantities of the clustering fluorescent dye that identify the two beads and clustering antibodies capable of binding to two different analytes of the plurality of analytes.

In some embodiments, the CBA event data is generated after associating the beads and the reporter antibodies with the plurality of analytes.

The method 800 proceeds from block 808 to block 812, where the computing system can: receive a user selection of a software program module capable of performing one or more steps performed by the processor.

In some embodiments, the computing system can: request a user selection of a CBA assay of a plurality of CBA assays for determining the quantities of the plurality analytes or a user input of the plurality of analytes. The processor can be programmed by the executable instructions to: receive the user selection of the CBA assay of the plurality of CBA assays for determining the quantities of the plurality analytes. The processor can be programmed by the executable instructions to: receive the user input of the plurality analytes.

In some embodiments, the computing system can: receive user selections of the reporter fluorescent dye and the clustering fluorescent dye.

In some embodiments, the computing system can: receive user selections of the standard CBA event data of the CBA event data corresponding to the plurality of standards. The computing system can: receive user selections of the sample CBA event data of the CBA event data corresponding to the plurality of samples and the standard CBA event data of the CBA event data corresponding to the plurality of standards.

In some embodiments, each of the plurality of events is associated with (3) a forward scatter value, and (4) a side scatter value in the CBA event data. The computing system can: determine a second plurality of gates for CBA event data, based on the forward scatter value and the side scatter value of each of the plurality of events, to determine the events of interest.

In some embodiments, the computing system can receive user inputs of an initial concentration and a dilution factor of each of the plurality of analytes.

In some embodiments, the computing system can receive a user selection of a regression function of a plurality of regression functions.

The method 800 proceeds to block 816, where the computing system determine a first plurality of gates for CBA event data, based on the clustering fluorescent intensity of each of the plurality of events, to determine events of interest and corresponding analytes.

The method 800 proceeds from block 816 to block 820, where the computing system for each of the plurality of analytes, determine a standard curve of correspondence of reporter fluorescent intensities and concentrations of the analyte using the initial concentration, the dilution factor, the regression function, and the reporter fluorescent intensities corresponding to the analyte in standard CBA event data of the CBA event data corresponding to the plurality of standards.

In some embodiments, to determine the standard curve, the computing system can: determine the standard curve of correspondence of the reporter fluorescent intensities and the concentrations of the analyte using the initial concentration, the dilution factor, the regression function, and median reporter fluorescent intensities corresponding to the analyte at different standard concentrations in the standard CBA event data of the CBA event data corresponding to the plurality of standards.

The method 800 proceeds to block 824, where the computing system can for each sample of a plurality of samples, determine a sample concentration of each of a plurality of analytes based on the reporter fluorescent intensity in the CBA event data corresponding to the analyte using the regression function. The computing system can generate (1) for each analyte of the plurality of analytes, a plot of the standard curve and the correspondence of the reporter fluorescent intensities and the concentrations of the analyte, and (2) a table comprising a sample concentration of each of the plurality of analytes for each of the plurality of samples.

In some embodiments, to determine the sample concentration, the computing system can: determine the sample concentration of each of a plurality of analytes based on a median reporter fluorescent intensity in the CBA event data corresponding to the analyte using the regression function. Two reporter fluorescent intensities of the reporter fluorescent dye associated with two events of the plurality of events can indicate quantities of two analytes of a plurality of analytes. Two different clustering fluorescent intensities of the clustering fluorescent dye associated with the two events of the plurality of events can identify the two analytes of the plurality of analytes.

In some embodiments, the computing system can: display visual indications corresponding to one or more steps performed by the processor. The computing system can: highlight a visual indication when performing the corresponding step. In some embodiments, the computing system can: generate output files of the plot and the table.

The method 800 ends at block 828.

Execution Environment

Figure 9:
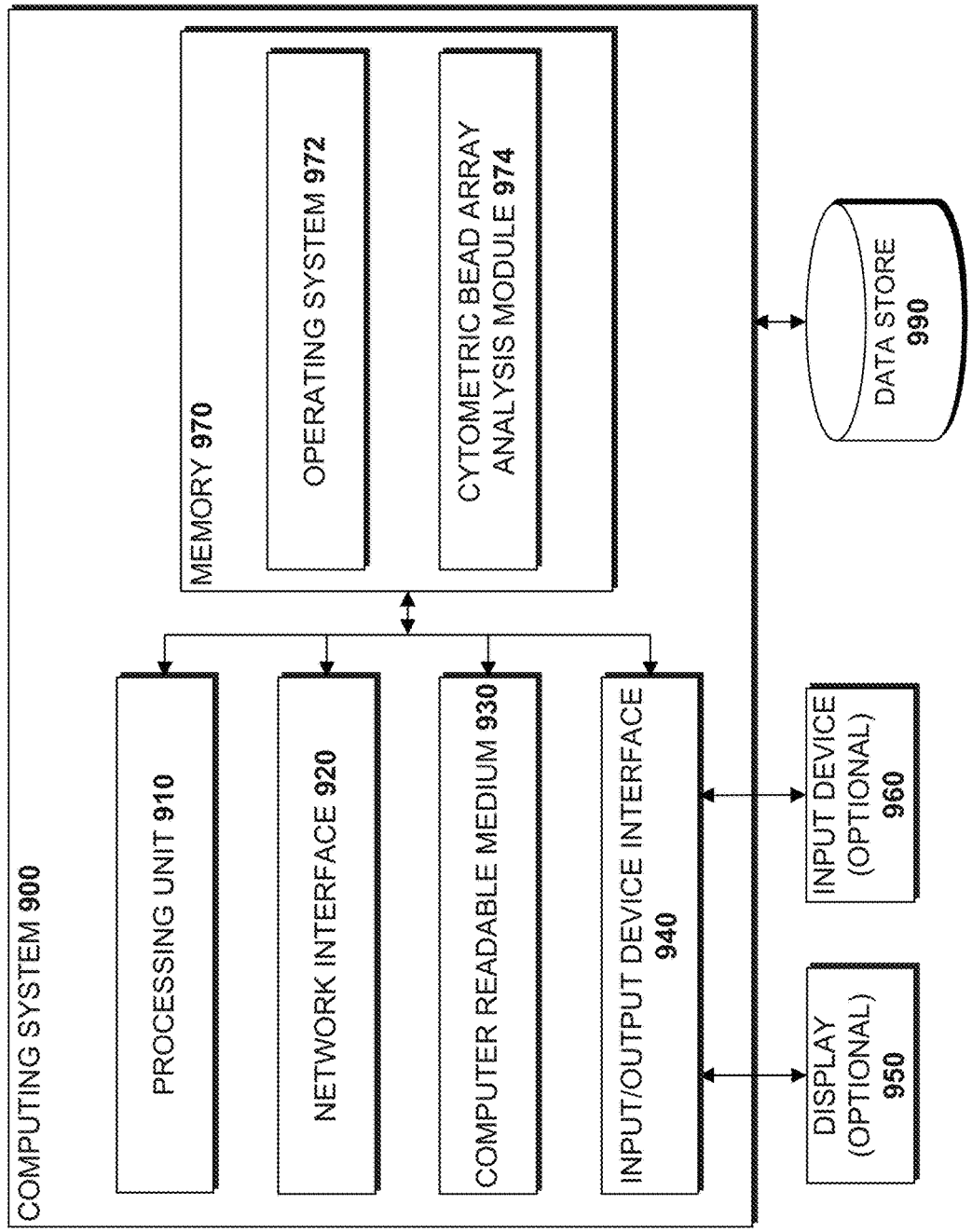
FIG. 9 is a block diagram of an illustrative computing system configured to implement cytometric bead array analysis.
Figure 10A:
Figure 10C:
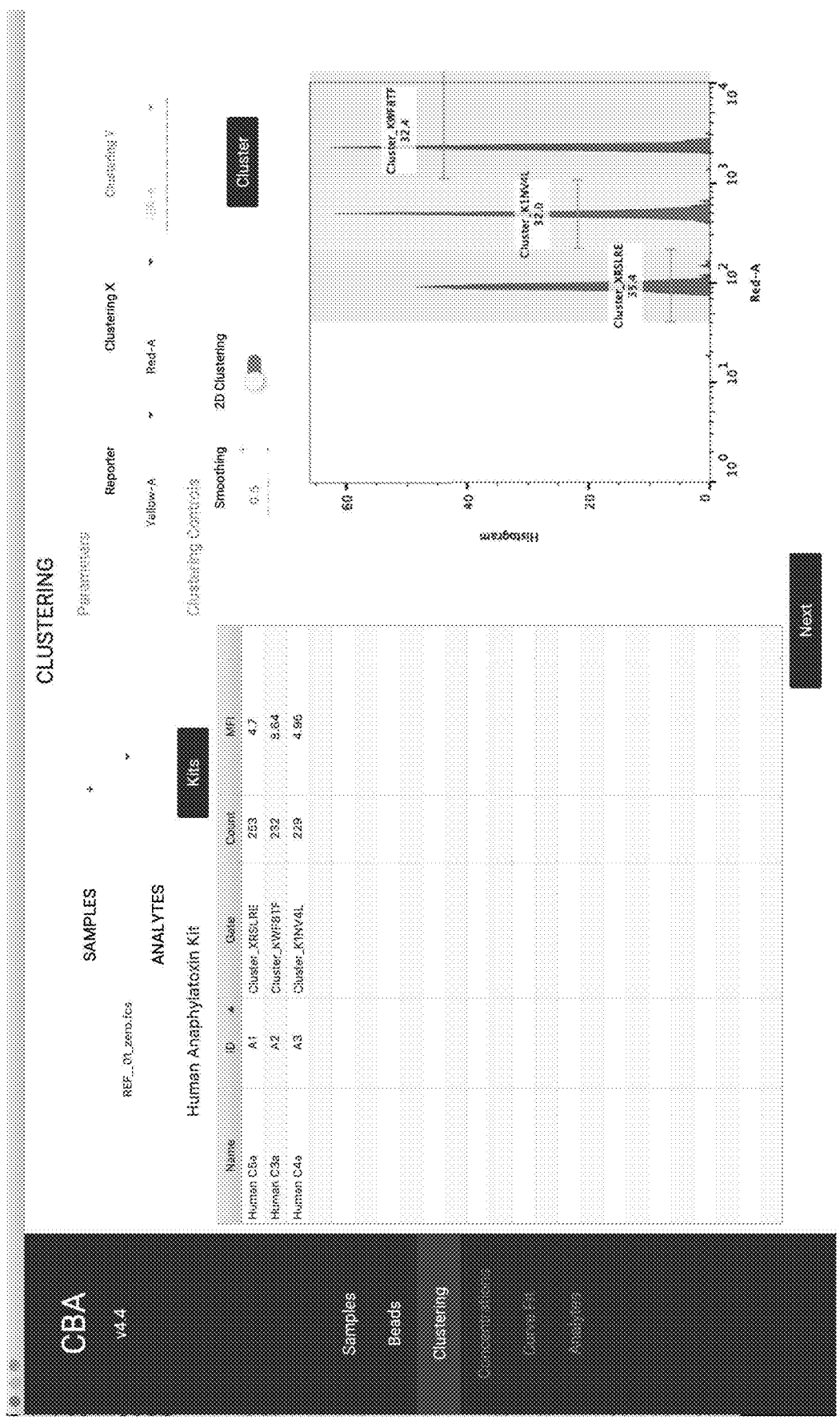
Figure 10D:
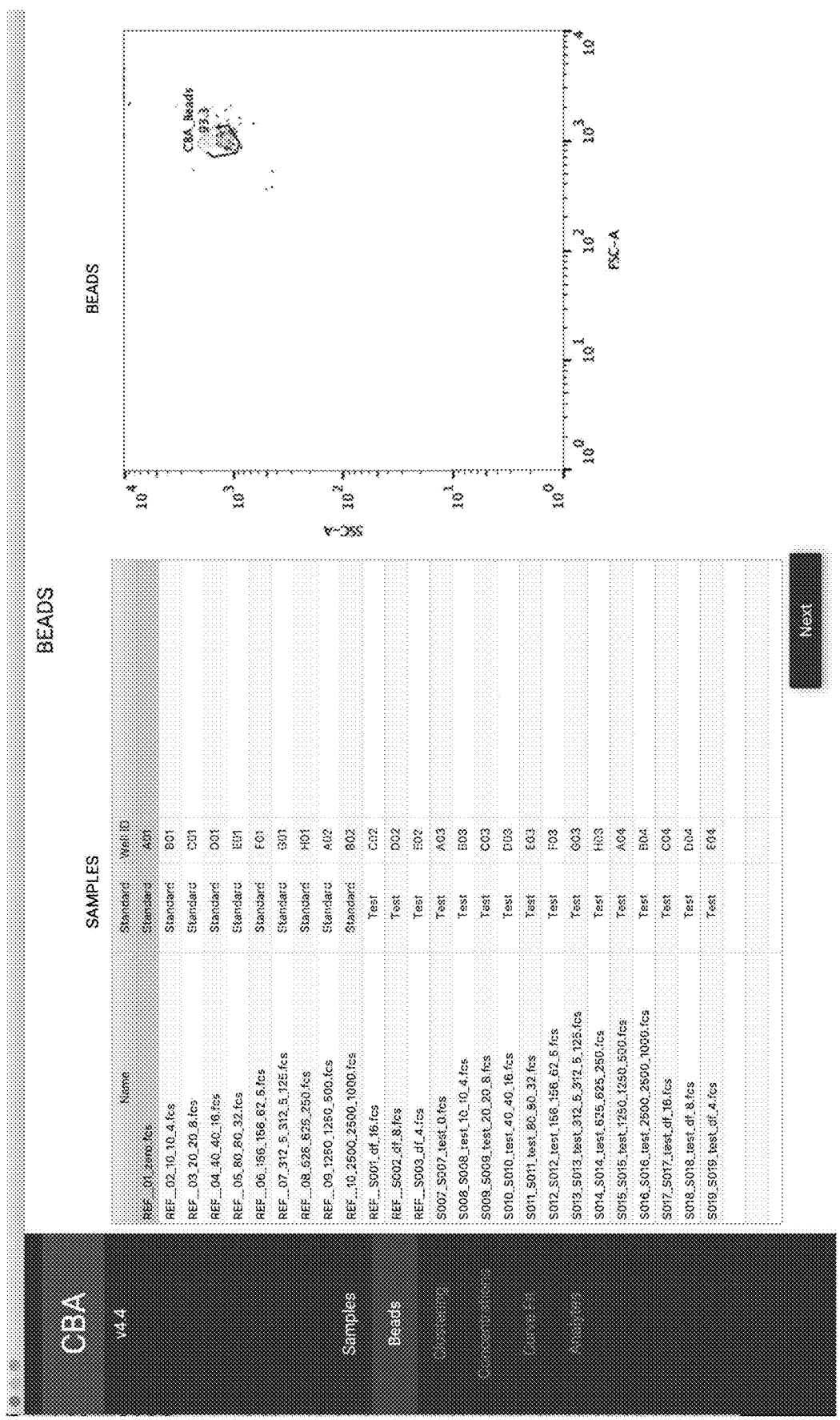
Figure 10E:
Figure 10F:
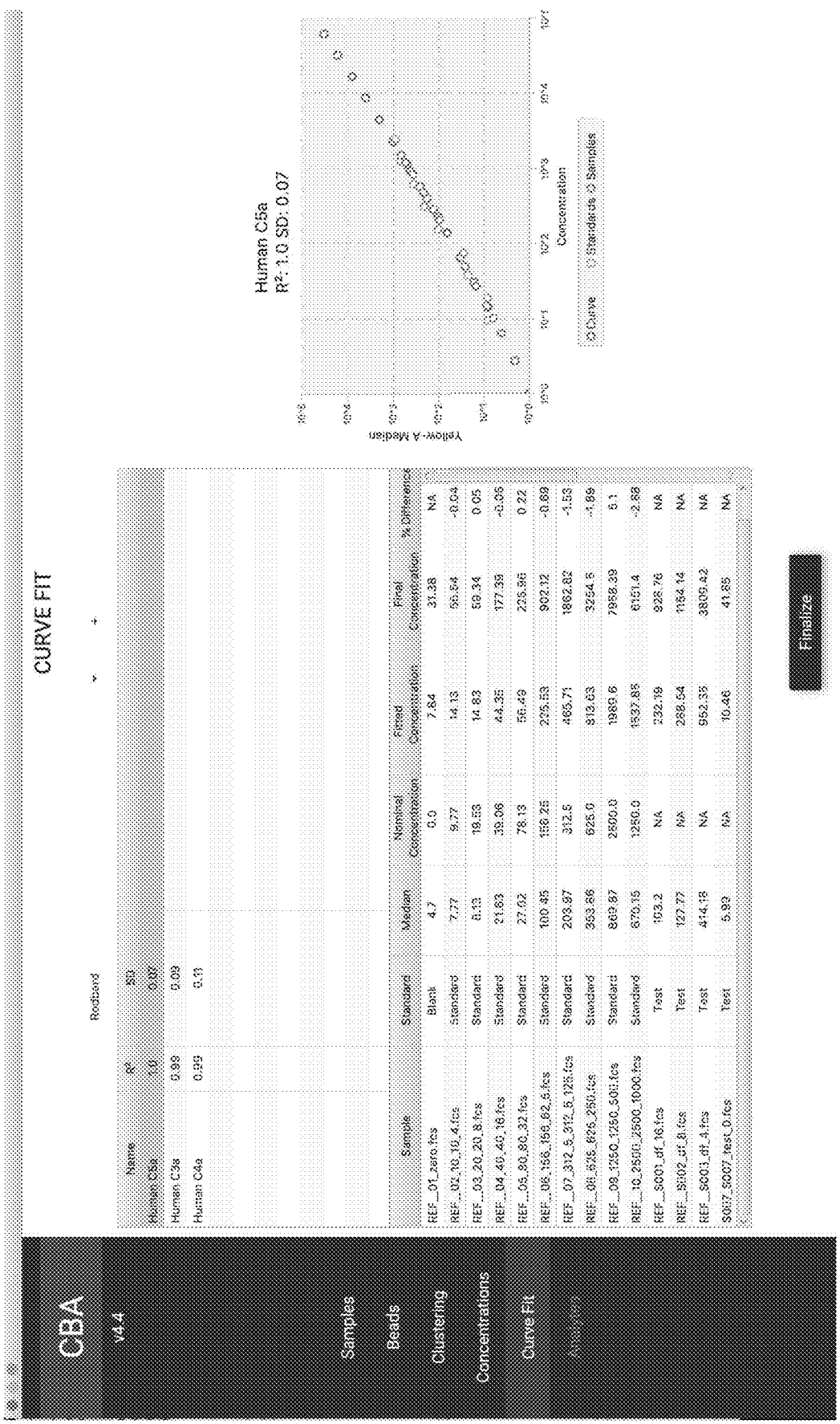
Figure 11A:
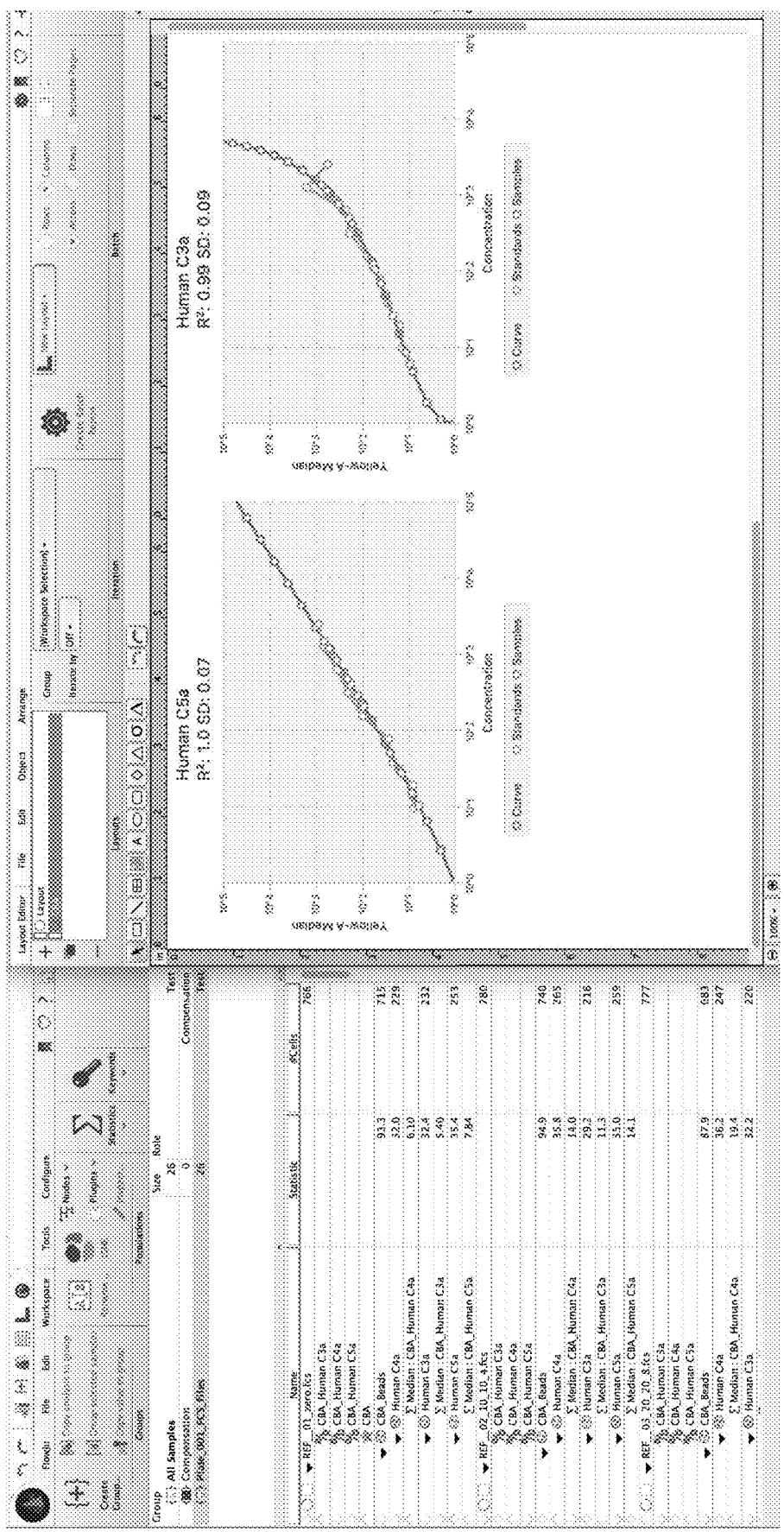
Figure 11B:
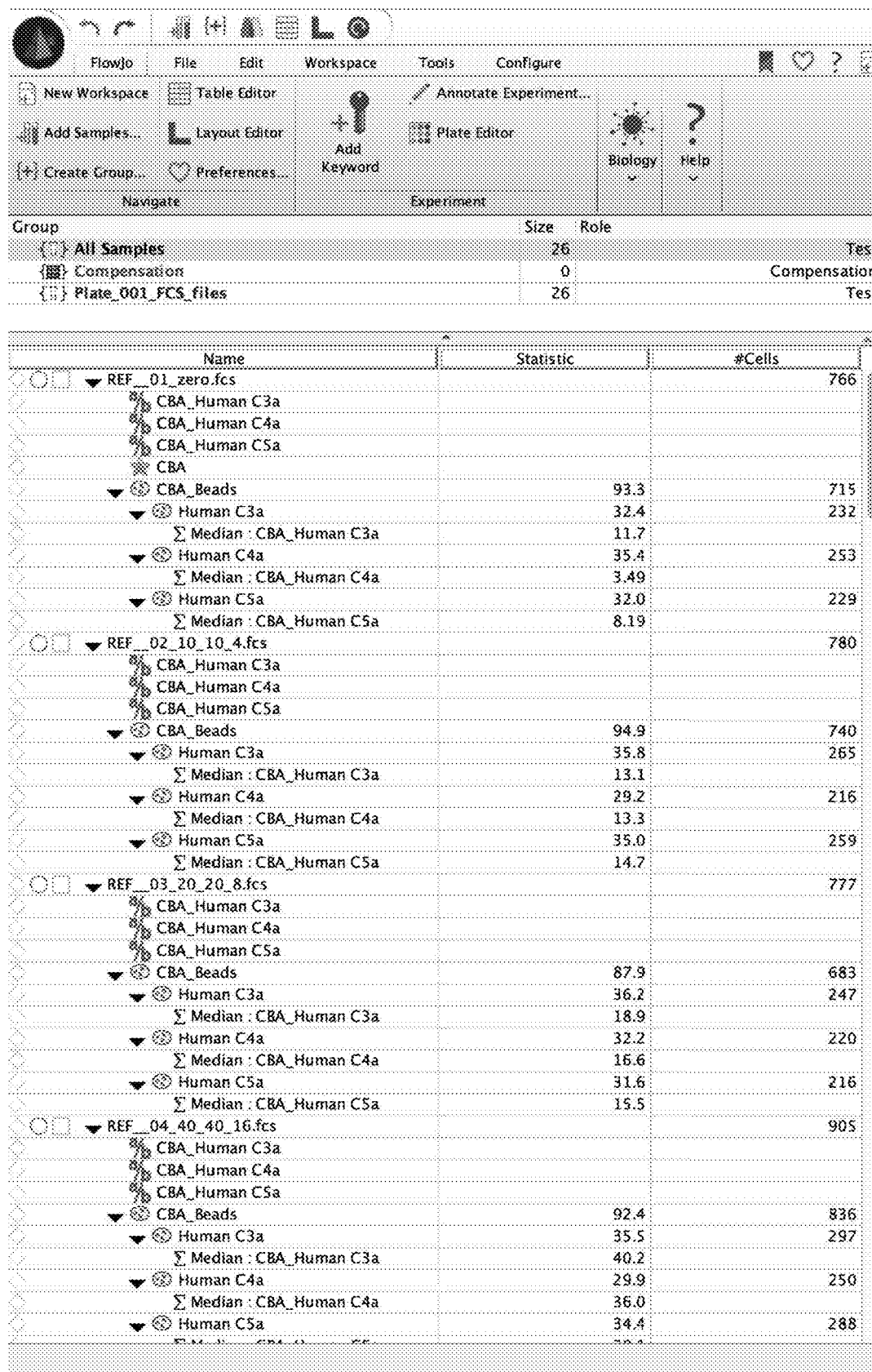
Figure 11C:
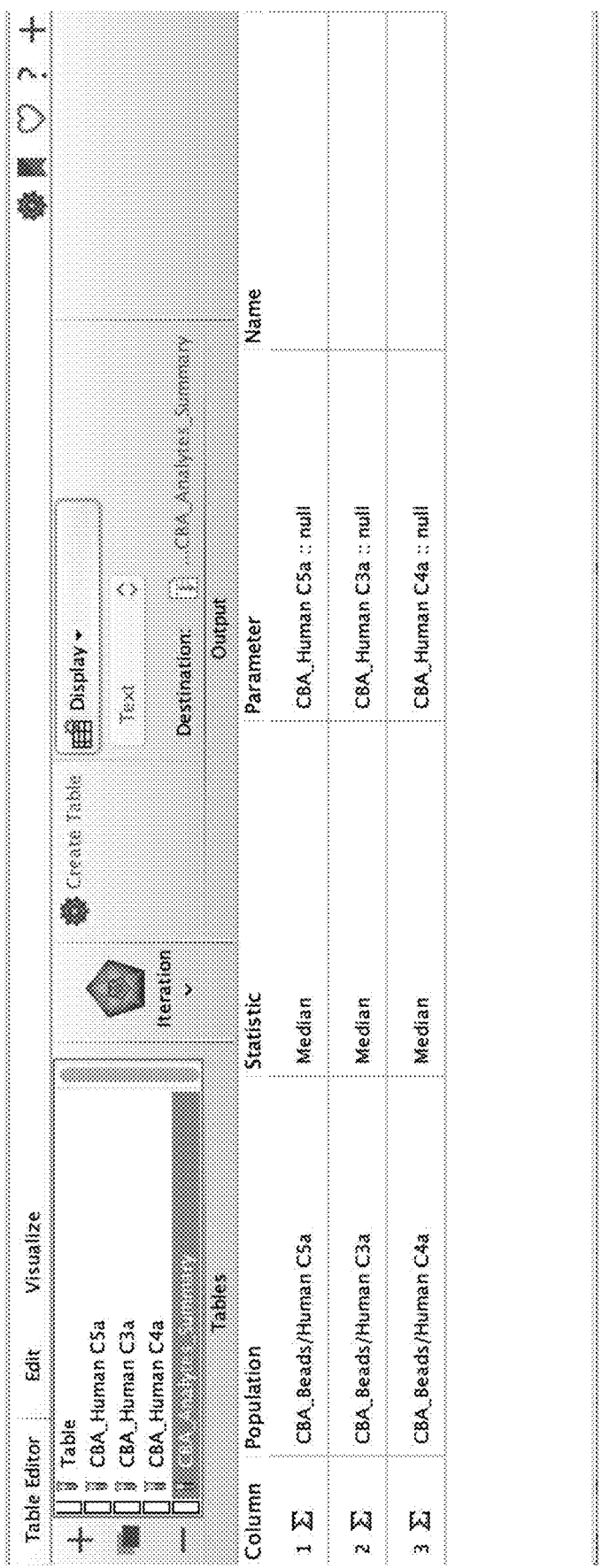
Figure 11E:
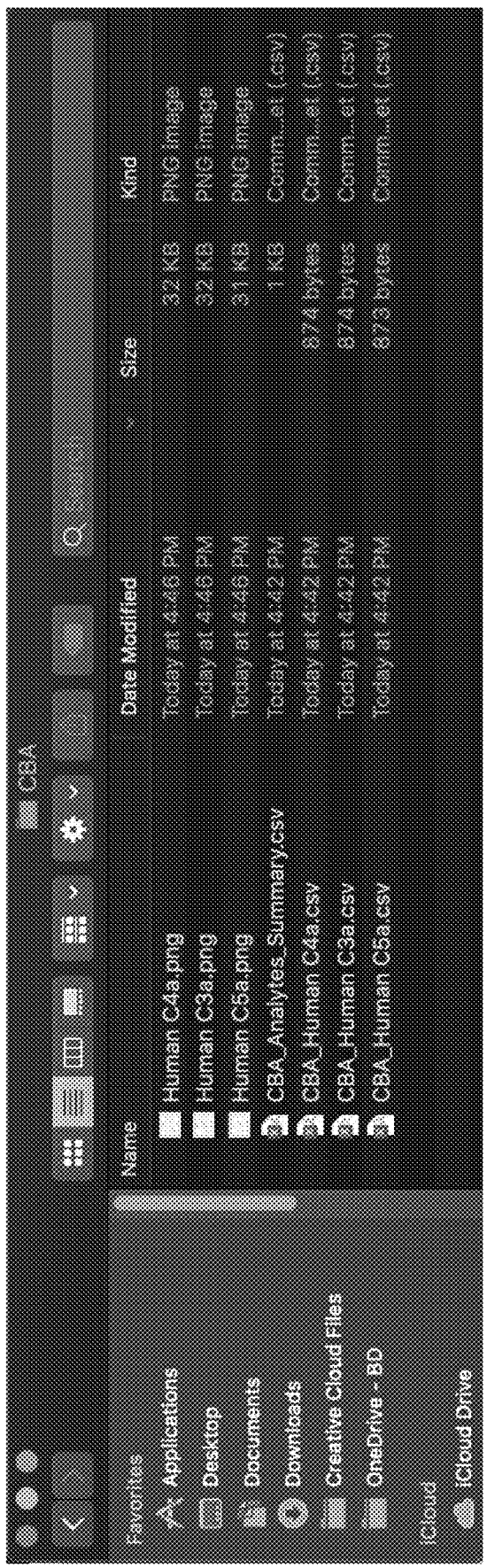

In FIG. 9 depicts a general architecture of an example computing device 900 configured to implement the metabolite, annotation and gene integration system disclosed herein. The general architecture of the computing device 900 depicted in FIG. 9 includes an arrangement of computer hardware and software components. The computing device 900 may include many more (or fewer) elements than those shown in FIG. 9. It is not necessary, however, that all of these generally conventional elements be shown in order to provide an enabling disclosure. As illustrated, the computing device 900 includes a processing unit 910, a network interface 920, a computer readable medium drive 930, an input/output device interface 940, a display 950, and an input device 960, all of which may communicate with one another by way of a communication bus. The network interface 920 may provide connectivity to one or more networks or computing systems. The processing unit 910 may thus receive information and instructions from other computing systems or services via a network. The processing unit 910 may also communicate to and from memory 970 and further provide output information for an optional display 950 via the input/output device interface 940. The input/output device interface 940 may also accept input from the optional input device 960, such as a keyboard, mouse, digital pen, microphone, touch screen, gesture recognition system, voice recognition system, gamepad, accelerometer, gyroscope, or other input device.

The memory 970 may contain computer program instructions (grouped as modules or components in some embodiments) that the processing unit 910 executes in order to implement one or more embodiments. The memory 970 generally includes RAM, ROM and/or other persistent, auxiliary or non-transitory computer-readable media. The memory 970 may store an operating system 972 that provides computer program instructions for use by the processing unit 910 in the general administration and operation of the computing device 900. The memory 970 may further include computer program instructions and other information for implementing aspects of the present disclosure.

For example, in one embodiment, the memory 970 includes a cytometric bead array analysis module 974 for performing cytometric bead analysis workflow, such as the analysis method 800 described with reference to FIG. 8. In addition, memory 970 may include or communicate with the data store 990 and/or one or more other data stores that the bead array data (such as cytometric bead array data) and the result of any analysis.

Terminology

As used herein, the terms "determine" or "determining" encompass a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing, and the like.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

As used herein, the term "message" encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

As used herein a "user interface" (also referred to as an interactive user interface, a graphical user interface or a UI) may refer to a network based interface including data fields, buttons, or other interactive controls for receiving input signals or providing electronic information or for providing information to the user in response to any received input signals. A UI may be implemented in whole or in part using technologies such as hyper-text mark-up language (HTML), JAVASCRIPT™, FLASH™, JAVA™, .NET™, WINDOWS OS™, macOS™, web services, or rich site summary (RSS). In some implementations, a UI may be included in a stand-alone client (for example, thick client, fat client) configured to communicate (e.g., send or receive data) in accordance with one or more of the aspects described.

As used herein a "data store" may be embodied in hard disk drives, solid state memories and/or any other type of non-transitory computer-readable storage medium accessible to or by a device such as an access device, server, or other computing device described. A data store may also or alternatively be distributed or partitioned across multiple local and/or remote storage devices as is known in the art without departing from the scope of the present disclosure. In yet other embodiments, a data store may include or be embodied in a data storage web service.

Those of skill in the art would understand that information, messages, and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill in the art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The techniques described herein may be implemented in hardware, software, firmware, or any combination thereof. Such techniques may be implemented in any of a variety of devices such as specifically programmed event processing computers, wireless communication devices, or integrated circuit devices. Any features described as modules or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials. The computer-readable medium may comprise memory or data storage media, such as random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable medium may be a non-transitory storage medium. The techniques additionally, or alternatively, may be realized at least in part by a computer-readable communication medium that carries or communicates program code in the form of instructions or data structures and that can be accessed, read, and/or executed by a computing device, such as propagated signals or waves.

The program code may be executed by a specifically programmed sort strategy processor, which may include one or more processors, such as one or more digital signal processors (DSPs), configurable microprocessors, an application specific integrated circuits (ASICs), field programmable gate arrays (FPGAs), or other equivalent integrated or discrete logic circuitry. Such a graphics processor may be specially configured to perform any of the techniques described in this disclosure. A combination of computing devices, e.g., a combination of a DSP and a microprocessor, a plurality of microprocessors, one or more microprocessors in conjunction with a DSP core, or any other such configuration in at least partial data connectivity may implement one or more of the features describe. In some aspects, the functionality described herein may be provided within dedicated software modules or hardware modules configured for encoding and decoding, or incorporated in a specialized sorting control card.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for cytometric bead array analysis for detecting analytes in a sample, comprising, in a flow cytometry data analysis workflow under control of a processor:
   receiving cytometric bead array (CBA) event data of a plurality of events corresponding to a plurality of samples and a plurality of standards, wherein each of the plurality of events is associated with (1) a reporter fluorescent intensity of a reporter fluorescent dye associated with a reporter antibody, (2) a clustering fluorescent intensity of a clustering fluorescent dye associated with a bead, (3) a forward scatter value, and (4) a side scatter value in the CBA event data, wherein the plurality of standards is associated with an initial concentration and a dilution factor of each of a plurality of analytes, wherein the CBA event data is generated by analyzing each of the plurality of samples suspected of comprising a plurality of analytes with a CBA assay for detecting the plurality of analytes and a particle analyzer;
   requesting a user selection of the CBA assay among a plurality of CBA assays for determining the quantities of the plurality analytes;
   receiving the user selection of the CBA assay;
   auto-gating to identify events in the CBA event data and corresponding analytes of the plurality of analytes based on:
      (I) the clustering fluorescent intensity of each of the plurality of events; or
      (II) the forward scatter value and the side scatter value of each of the plurality of events;
   receiving a user selection of a regression function of a plurality of regression functions;
   for each of the plurality of analytes, determining a standard curve of correspondence of reporter fluorescent intensities and concentrations of the analyte using the initial concentration, the dilution factor, the regression function, and the reporter fluorescent intensities corresponding to the analyte in standard CBA event data of the CBA event data corresponding to the plurality of standards;
   for each sample of the plurality of samples, determining a sample concentration of each of the plurality of analytes based on the reporter fluorescent intensity in sample CBA event data of the CBA event data corresponding to the analyte using the regression function;
   generating (1) for each analyte of the plurality of analytes, a plot of the standard curve and the correspondence of the reporter fluorescent intensities and the concentrations of the analyte, and (2) a table comprising: the sample concentration of each of the plurality of analytes for each of the plurality of samples; and an identity of each of the plurality of analytes for each of the plurality of samples provided by the user selection of the CBA assay; and
   displaying the plot and the table.

2. The method of claim 1, further comprising: receiving user selections of the reporter fluorescent dye and the clustering fluorescent dye.

3. The method of claim 2, comprising receiving the user selection of the regression function only after receiving user selections of the reporter fluorescent dye and the clustering fluorescent dye.

4. The method of claim 1, further comprising: receiving user inputs of the initial concentration and the dilution factor of each of the plurality of analytes.

5. The method of claim 4, comprising receiving the user selection of the regression function only after receiving user inputs of the initial concentration and the dilution factor of each of the plurality of standards.

6. The method of claim 1, wherein a sample of the plurality of samples comprises the plurality of analytes each at a sample concentration, wherein a standard of the plurality of standards comprises each of the plurality of analytes each at a standard concentration, and wherein two standards of the plurality of standards comprise two different standard concentrations of each of the plurality of analytes.

7. The method of claim 1, comprising: receiving user selections of the standard CBA event data of the CBA event data corresponding to the plurality of standards.

8. The method of claim 1, comprising: receiving user selections of the sample CBA event data of the CBA event data corresponding to the plurality of samples and the standard CBA event data of the CBA event data corresponding to the plurality of standards.

9. The method of claim 1, wherein the bead is associated with a clustering antibody capable of binding to an analyte of the plurality of analytes.

10. The method of claim 9, wherein two beads of the beads comprise different (1) quantities of the clustering fluorescent dye that identify the two beads and (2) clustering antibodies capable of binding to two different analytes of the plurality of analytes.

11. The method of claim 1, comprising: associating the beads and the reporter antibodies with the plurality of analytes.

12. The method of claim 1, wherein determining the standard curve comprises: determining the standard curve of correspondence of the reporter fluorescent intensities and the concentrations of the analyte using the initial concentration, the dilution factor, the regression function, and median reporter fluorescent intensities corresponding to the analyte at different standard concentrations in the standard CBA event data of the CBA event data corresponding to the plurality of standards.

13. The method of claim 1, wherein determining the sample concentration comprises determining the sample concentration of each of a plurality of analytes based on a median reporter fluorescent intensity in the CBA event data corresponding to the analyte using the regression function.

14. The method of claim 1, wherein two reporter fluorescent intensities of the reporter fluorescent dye associated with two events of the plurality of events indicate quantities of two analytes of a plurality of analytes, wherein two different clustering fluorescent intensities of the clustering fluorescent dye associated with the two events of the plurality of events identify the two analytes of the plurality of analytes.

15. The method of claim 1, wherein each of the plurality of events is associated with a combination of clustering fluorescent intensities of at least two clustering fluorescent dyes associated with the bead in the CBA event data, and wherein two different combinations of clustering fluorescent intensities of the at least two clustering fluorescent dyes associated with the two events of the plurality of events identify the two analytes of the plurality of analytes.

16. The method of claim 1, comprising receiving user inputs of the identities of the plurality of analytes detectable by the CBA assay, the user inputs comprising an identity of an analyte associated with the bead.

17. The method of claim 1, wherein requesting the user selection is performed after receiving the CBA event data.

18. A method for cytometric bead array analysis for detecting analytes in a sample, comprising, in a flow cytometry data analysis workflow under control of a processor and through one or more user interfaces:

(a) receiving cytometric bead array (CBA) event data of a plurality of events corresponding to a plurality of samples and a plurality of standards, wherein each of the plurality of events is associated with (1) a reporter fluorescent intensity of a reporter fluorescent dye associated with a reporter antibody, (2) a clustering fluorescent intensity of a clustering fluorescent dye associated with a bead, (3) a forward scatter value, and (4) a side scatter value in the CBA event data, wherein the plurality of standards is associated with an initial concentration and a dilution factor of each of a plurality of analytes, wherein the CBA event data is generated by analyzing each of the plurality of samples suspected of comprising one or more of the plurality of analytes with a CBA assay for detecting the plurality of analytes and a particle analyzer, wherein receiving CBA event data comprises receiving user selections of sample CBA event data of the CBA event data corresponding to the plurality of samples and standard CBA event data of the CBA event data corresponding to the plurality of standards;

(b) requesting a user selection of the CBA assay among a plurality of CBA assays for determining the quantities of the plurality analytes;

(c) receiving the user selections of the CBA assay;

(d) receiving user selections of the reporter fluorescent dye and the clustering fluorescent dye;

(e) auto-gating to identify events in the CBA event data and corresponding analytes of the plurality of analytes based on:

(I) the clustering fluorescent intensity of each of the plurality of events; or (II) the forward scatter value and the side scatter value of each of the plurality of events;

(f) receiving user inputs of the initial concentration and the dilution factor of each of the plurality of standards;

(g) receiving a user selection of a regression function of a plurality of regression functions only after (f);

(h) for each of the plurality of analytes, determining a standard curve of correspondence of reporter fluorescent intensities and concentrations of the analyte using the initial concentration, the dilution factor, the regression function, and the reporter fluorescent intensities corresponding to the analyte in standard CBA event data of the CBA event data corresponding to the plurality of standards;

(i) for each sample of the plurality of samples, determining a sample concentration of each of the plurality of analytes based on the reporter fluorescent intensity in sample CBA event data of the CBA event data corresponding to the analyte using the regression function;

(j) generating (1) for each analyte of the plurality of analytes, a plot of the standard curve and the correspondence of the reporter fluorescent intensities and the concentrations of the analyte, and (2) a table comprising: the sample concentration of each of the plurality of analytes for each of the plurality of samples; and an identity of each of the plurality of analytes for each of the plurality of samples provided by the user selection of the CBA assay; and (k) displaying the plot and the table.

19. The method of claim 18, wherein (b) is performed after (a).